(12) United States Patent
Kimura et al.

(10) Patent No.: US 11,392,808 B2
(45) Date of Patent: Jul. 19, 2022

(54) PAPER MANAGEMENT SYSTEM, PAPER MANAGEMENT METHOD, AND PRINT CONTROL APPARATUS

(71) Applicant: CANON KABUSHIKI KAISHA, Tokyo (JP)

(72) Inventors: Yusuke Kimura, Abiko (JP); Yuzo Harano, Sagamihara (JP); Hideaki Ooba, Yokohama (JP); Aya Ito, Tokyo (JP); Nobuhiro Kawamura, Nagareyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/159,366

(22) Filed: Oct. 12, 2018

(65) Prior Publication Data

US 2019/0114519 A1    Apr. 18, 2019

(30) Foreign Application Priority Data

Oct. 18, 2017  (JP) .............................. JP2017-202093

(51) Int. Cl.
| | | |
|---|---|---|
| *H04N 1/40* | (2006.01) | |
| *G06K 15/00* | (2006.01) | |
| *G01N 33/34* | (2006.01) | |
| *B41J 11/00* | (2006.01) | |
| *G06K 15/16* | (2006.01) | |
| *B41J 11/48* | (2006.01) | |

(52) U.S. Cl.
CPC ......... *G06K 15/4065* (2013.01); *B41J 11/003* (2013.01); *B41J 11/485* (2013.01); *G01N 33/346* (2013.01); *G06K 15/005* (2013.01); *G06K 15/16* (2013.01)

(58) Field of Classification Search
CPC .. G06K 15/4065; G06K 15/005; G06K 15/16; H41J 11/003; B41J 11/485; G01N 33/346
USPC ................................................. 358/442, 1.12
See application file for complete search history.

(56) References Cited

U.S. PATENT DOCUMENTS

| | | | |
|---|---|---|---|
| 2003/0160774 A1 | 8/2003 | Minagawa | |
| 2005/0031392 A1* | 2/2005 | Yamamoto | ............. B41J 11/009 400/62 |
| 2007/0263242 A1 | 11/2007 | Takahashi | |
| 2009/0316184 A1 | 12/2009 | Ohyama | |
| 2012/0105879 A1* | 5/2012 | Tanaka | ............... H04N 1/00482 358/1.9 |
| 2013/0201520 A1 | 8/2013 | Sato | |
| 2019/0037087 A1* | 1/2019 | Kawaguchi | .......... H04N 1/0044 |

(Continued)

FOREIGN PATENT DOCUMENTS

| | | |
|---|---|---|
| JP | 2000-025293 A | 1/2000 |
| JP | 2007-301911 A | 11/2007 |

(Continued)

*Primary Examiner* — Cheukfan Lee
(74) *Attorney, Agent, or Firm* — Canon U.S.A., Inc. I.P. Division

(57) ABSTRACT

A paper management system setting a paper information piece of paper stored in a sheet feeding unit in an image forming apparatus from a list of paper information pieces registers the paper information pieces with a favorite group, displays a list of the paper information pieces for each favorite group, and enables the list of the paper information pieces to be associated with a paper feed unit through the screen displaying the list.

14 Claims, 32 Drawing Sheets

(56) References Cited

U.S. PATENT DOCUMENTS

2020/0004472 A1* 1/2020 Kimura ................ G06F 3/1232
2020/0225887 A1* 7/2020 Ito ........................ G06F 3/1208

FOREIGN PATENT DOCUMENTS

| JP | 2009-286577 A | 12/2009 |
| JP | 2011-113146 A | 6/2011 |
| JP | 2014205343 A | 10/2014 |
| JP | 2017-097595 A | 6/2017 |
| KR | 2010-0123003 A | 11/2010 |

* cited by examiner

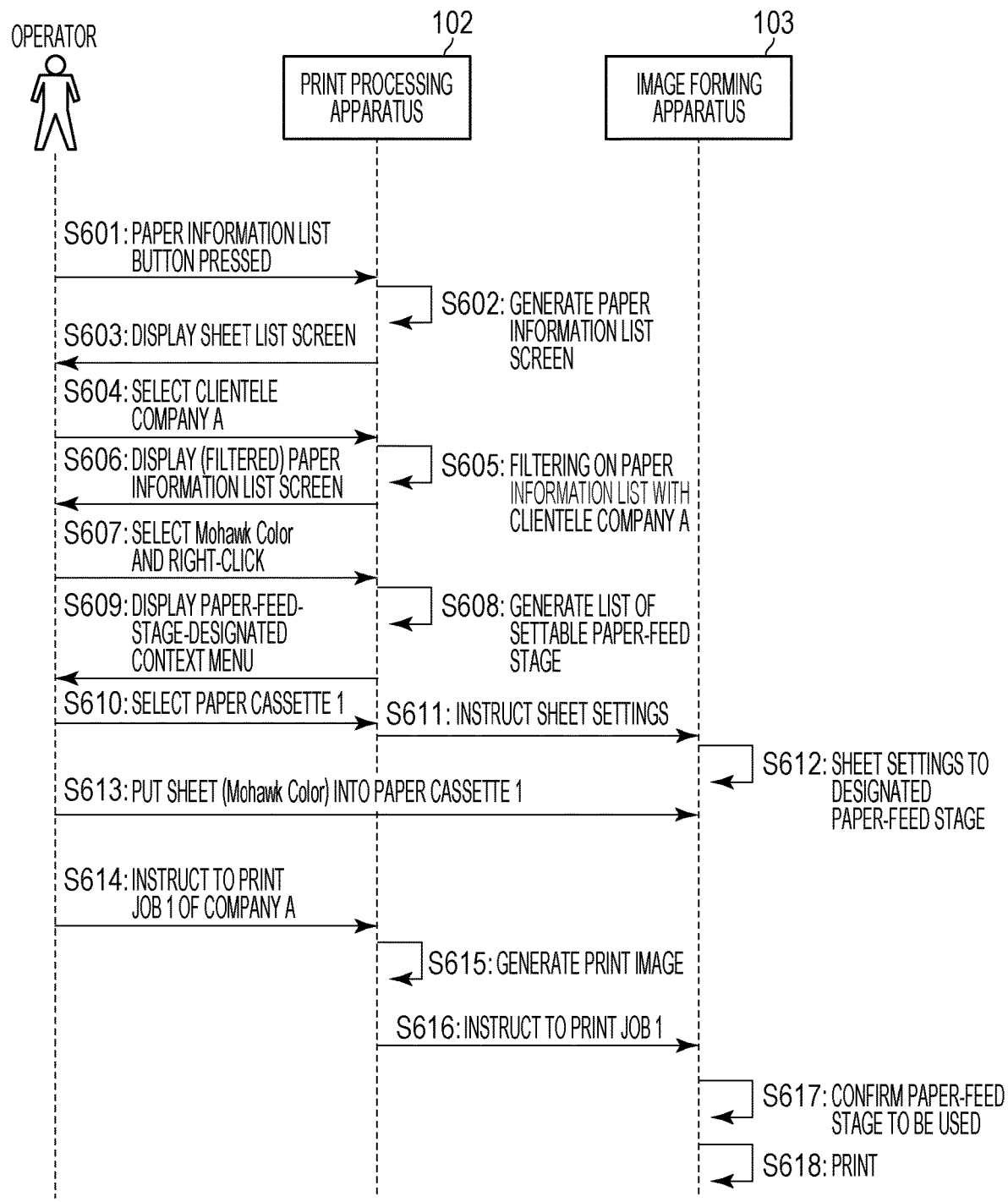

FIG. 7B

| ADJUSTMENT: | | DISPLAY GROUP: ALL |
|---|---|---|
| ADJUSTMENT ITEMS | NECESSITY OF ADJUSTMENT | DISPLAY GROUP |
| GLOSSINESS/BLACK QUALITY ADJUSTMENT | NO | QUALITY |
| ADJUSTMENT OF SECONDARY TRANSFER VOLTAGE | NO | QUALITY |
| WHITE VOID AT BACK END | NO | QUALITY |
| ADJUSTMENT OF SECONDARY TRANSFER ANTISTATIC BIAS | NO | QUALITY |
| ITB IMAGE REMOVAL ADJUSTMENT | NO | QUALITY |
| TONER AMOUNT ADJUSTMENT MODE | NO | QUALITY |
| ADJUSTMENT OF PRIMARY TRANSFER VOLTAGE | NO | QUALITY |
| ADJUSTMENT OF REGISTRATION LOOP AMOUNT | NO | QUALITY |
| REGISTRATION SPEED ADJUSTMENT | NO | QUALITY |
| SMEARING CORRECTION | NO | QUALITY |
| FIXING PRESSURE ADJUSTMENT | NO | QUALITY |
| FIXING SPEED ADJUSTMENT | NO | QUALITY |
| IMAGE POSITION ADJUSTMENT | NO | IMAGE POSITION |
| LEADING/TRAILING EDGE MARGIN ADJUSTMENT | NO | IMAGE POSITION |
| HORIZONTAL REGISTRATION AUTOMATIC ADJUSTMENT | NO | IMAGE POSITION |
| SHEET SORTING FAN AIRFLOW ADJUSTMENT | NO | SHEET CONVEYANCE |
| PRE-FIXING CONVEYING FAN AIRFLOW ADJUSTMENT | NO | SHEET CONVEYANCE |

*NAME: CLIENTELE COMPANY A_BODY: PAPER 1
COLOR: WHITE
*GRAMMAGE: 100 g/m²
*SURFACE PROPERTY: HIGH QUALITY PAPER
*SIZE: A4
  X: mm (148.0~762.0)
  Y: mm (100.0~330.2) INCH
FEATURE: NONE
ENVELOP FLAP POSITION:
DOUBLE SIDED/SECOND TIME:
  ● NOT SET
  ○ SET
FAVORITES:
  ☐ ① CLIENTELE COMPANY A
  ☐ ② CLIENTELE COMPANY B
  ☐ ③ CLIENTELE COMPANY C
REGISTER/EDIT...
*REQUIRED.

OK 756
CANCEL 757

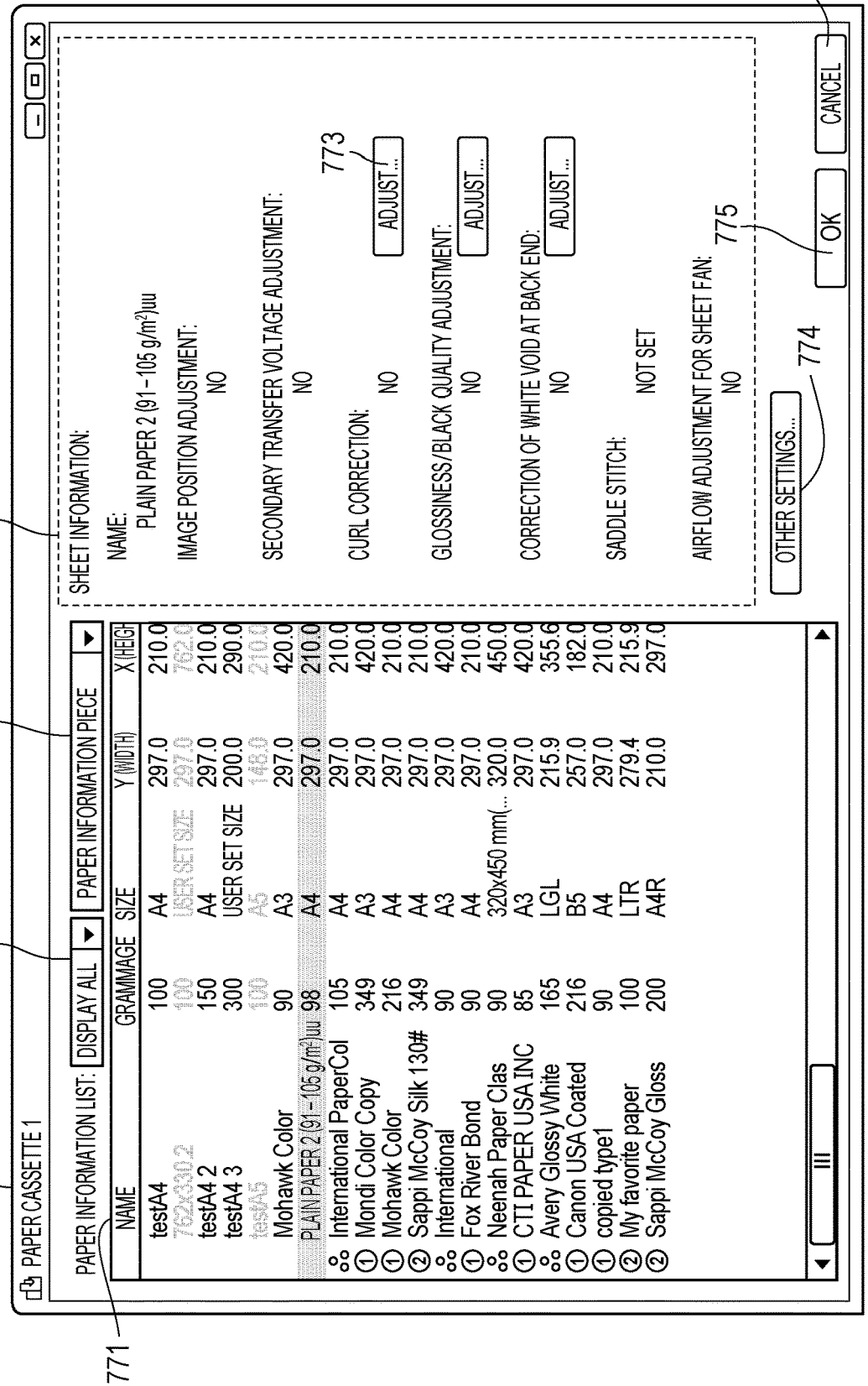

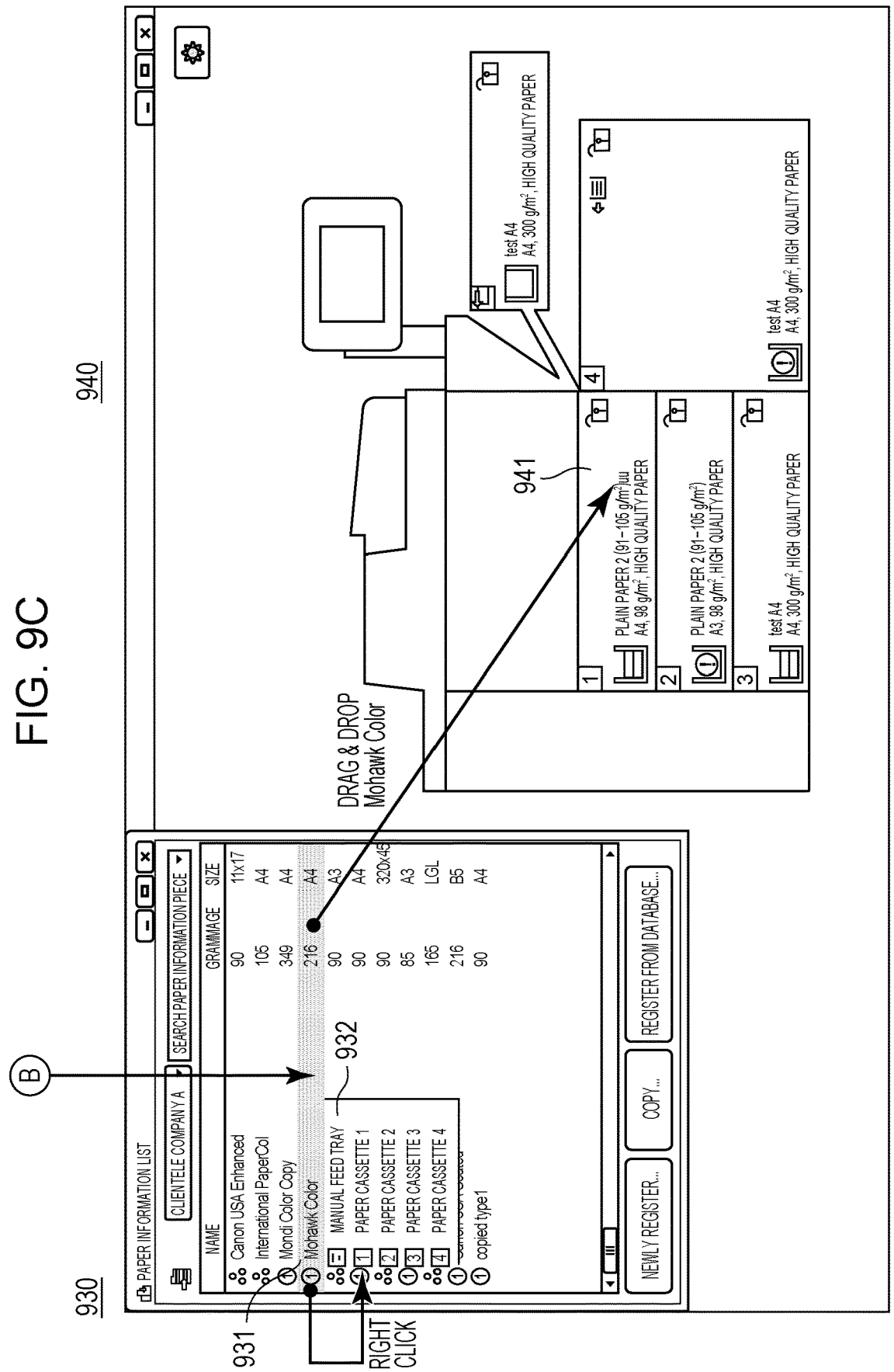

| PAPER INFORMATION LIST | | | |
|---|---|---|---|
| DISPLAY ALL ▼ | SEARCH PAPER INFORMATION PIECE ▼ | | |

DISPLAY ALL
CLIENTELE COMPANY A
CLIENTELE COMPANY B
CLIENTELE COMPANY C
LOG

| | NAME | GRAMMAGE | SIZE |
|---|---|---|---|
| ⚬⚬ | Canon US | 90 | 11x1 |
| ② | Neenah B | 120 | A4R |
| ⚬⚬ | International PaperCol | 105 | A4 |
| ① | Mondi Color Copy | 349 | A4 |
| ① | Mohawk Color | 216 | A4 |
| ② | Sappi McCoy Silk 130# | 349 | A3 |
| ⚬⚬ | International | 90 | A3 |
| ① | Fox River Bond | 90 | A4 |
| ⚬⚬ | Neenah Paper Clas | 90 | 320> |
| ① | CTI PAPER USA INC | 85 | A3 |
| | Avery Glossy White | 165 | LGL |
| ① | Canon USA Coated | 216 | B5 |
| ① | copied type1 | 90 | A4 |
| ② | My favorite paper | 100 | LTR |
| ② | Sappi McCoy Gloss | 200 | A4R |

1011 → (Avery Glossy White row)

[ NEWLY REGISTER... ] [ COPY... ] [ REGISTER FROM DATABASE... ]

RIGHT CLICK
FAVORITES ICON
③

| PAPER INFORMATION LIST | | | |
|---|---|---|---|
| DISPLAY ALL ▼ | SEARCH PAPER INFORMATION PIECE ▼ | | |
| DISPLAY ALL | | | |
| CLIENTELE COMPANY A | | | |
| NAME — CLIENTELE COMPANY B | | GRAMMAGE | SIZE |
| Canon US CLIENTELE COMPANY C | | 90 | 11x1 |
| Neenah B LOG | | 120 | A4R |
| International PaperCol | | 105 | A4 |
| Mondi Color Copy | | 349 | A4 |
| Mohawk Color | | 216 | A4 |
| Sappi McCoy Silk 130# | 1021 | 349 | A3 |
| International | | 90 | A3 |
| ☑ ① CLIENTELE COMPANY A | | 90 | A4 |
| ☑ ② CLIENTELE COMPANY B | | 90 | 320> |
| ☐ ③ CLIENTELE COMPANY C | | 85 | A3 |
| Avery Glossy White | | 165 | LGL |
| Canon USA Coated | | 216 | B5 |
| copied type1 | | 90 | A4 |
| My favorite paper | | 100 | LTR |
| Sappi McCoy Gloss | | 200 | A4R |

C

| NEWLY REGISTER... | COPY... | REGISTER FROM DATABASE... |

| NAME OF PAPER | PAPER ID | FAVORITE ID | USAGE HISTORY | SIZE | GRAMMAGE | SETTABLE PAPER FEED TRAY ID |
|---|---|---|---|---|---|---|
| Mohawk Color | 1 | 1 | 123 | A4 | 216 | 1,2,3,4,5 |
| Avery Glossy White | 2 | 1,2 | 111 | LGL | 165 | 1,2,3,4,5 |
| PLAIN PAPER 2 (91–105 g/m$^2$)uu | 3 | NOT SET | 50 | A4 | 105 | 1,2,3,4,5 |
| PLAIN PAPER 2 (91–105 g/m$^2$) | 4 | NOT SET | 11 | A3 | 105 | 1,2,3,4,5 |
| test A4 | 5 | 3 | 21 | A4 | 300 | 1,2,3,4,5 |
| ..... | ..... | ..... | ..... | ..... | ..... | ..... |

| NAME OF PAPER FEED STAGE | PAPER FEED STAGE ID | PAPER ID | REMAINED NUMBER OF SHEETS |
|---|---|---|---|
| PAPER CASSETTE 1 | 1 | 3 | 75 |
| PAPER CASSETTE 2 | 2 | 4 | 0 |
| PAPER CASSETTE 3 | 3 | 5 | 25 |
| PAPER CASSETTE 4 | 4 | 5 | 0 |
| MANUAL FEED TRAY | 5 | 5 | 100 |
| .... | .... | .... | .... |

| NAME OF FAVORITE | FAVORITE ID | ICON ID |
|---|---|---|
| CLIENTELE COMPANY A | 1 | 1 |
| CLIENTELE COMPANY B | 2 | 2 |
| CLIENTELE COMPANY C | 3 | 3 |
| .... | .... | .... |

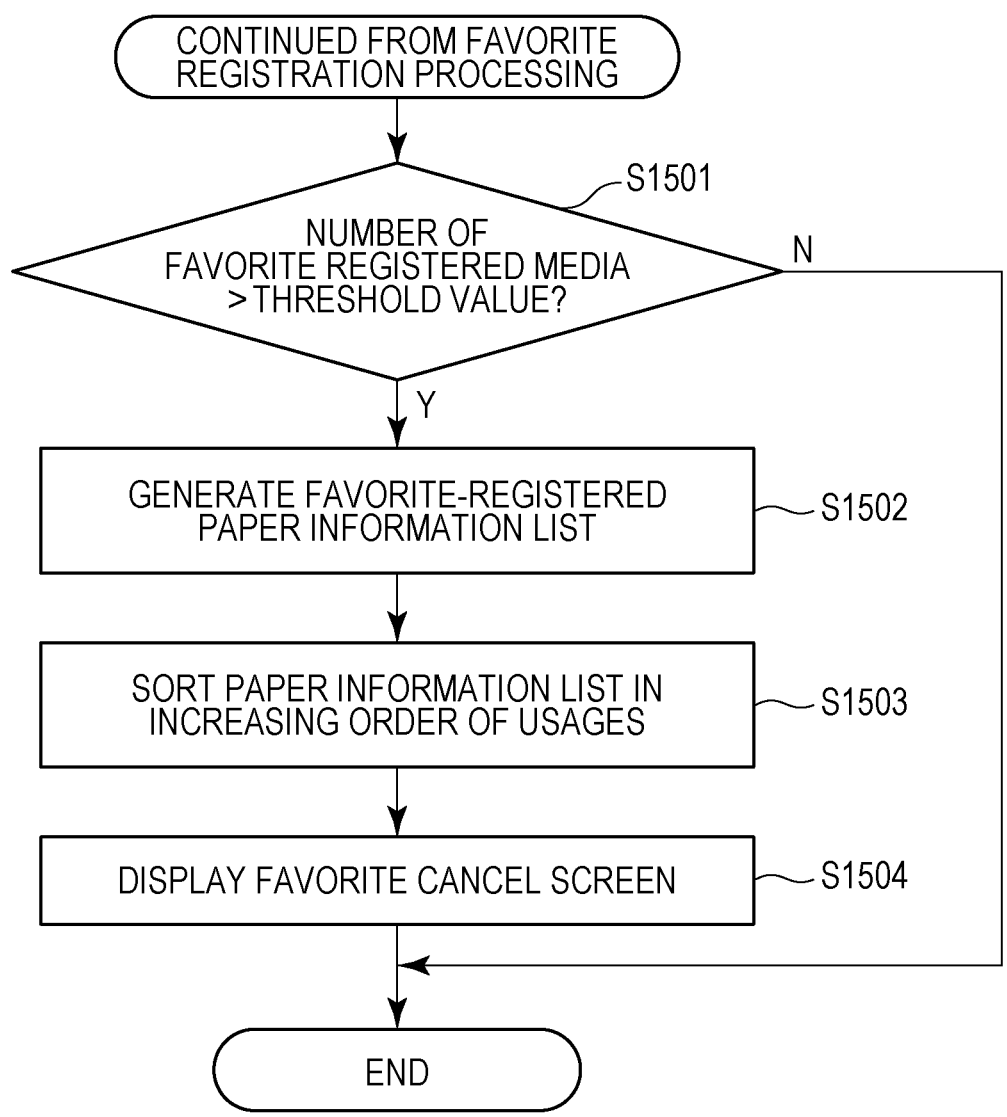

| PAPER INFORMATION LIST | | |
|---|---|---|
| DISPLAY ALL ▼ | SEARCH PAPER INFORMATION PIECE ▼ | |

1611

| | NAME | GRAMMAGE | SIZE |
|---|---|---|---|
| ● | International Paper abcdefg | 100 | STMTR |
| | Favorite paper | 200 | STMTR |
| | International PaperC | 162 | B5 |
| | International PaperH | 80 | USER |
| | Neenah Paper Classsic | 91 | A3 |
| ① | Canon USA Enhanced | 90 | 11x17 |
| ① | Neenah Exact Color | 120 | A4R |
| ① | International PaperCol | 105 | A4 |
| ① | Mondi Color Copy | 349 | A4 |
| ① | Mohawk Color | 216 | A4 |
| ① | Sappi McCoy Silk 130# | 349 | A3 |
| ① | International | 90 | A3 |
| | Fox River Bond1 | 90 | A4 |
| | Neenah Paper Clas | 90 | 320x45 |
| ① | CTI PAPER USA INC | 85 | A3 |
| ① | Avery Glossy White | 165 | LGL |
| | Canon USA Coated | 216 | B5 |
| ① | Copied type1 | 90 | A4 |

[ NEWLY REGISTER... ] [ COPY... ] [ REGISTER FROM DATABASE... ]

PAPER MANAGEMENT SYSTEM, PAPER MANAGEMENT METHOD, AND PRINT CONTROL APPARATUS

BACKGROUND OF THE INVENTION

Field of the Invention

The present disclosure relates to a system configured to manage paper information to be used for printing.

Description of the Related Art

Conventionally, an apparatus such as a printer has been known as an image forming apparatus configured to form an image on paper (or sheet). As one of such image forming apparatuses, an image forming apparatus (such as Japanese Patent Laid-Open No. 2014-205343) has been known which is configured to supply paper based on paper information added to print data. In the image forming apparatus, paper information piece is to be associated in advance with a paper-feed stage, and a user may search and designate a paper information piece associated with the paper-feed stage from a list of registered paper information pieces.

SUMMARY OF THE INVENTION

A paper management system defining paper information relating to paper stored in a sheet feeding unit in an image forming apparatus, the paper management system being capable of causing a display device to display a screen containing a list of paper information pieces belonging to a specific group, the paper management system include a unit configured to register a paper information piece designated among a plurality of paper information pieces with a group designated among a plurality of groups at least including a first group and a second group, a unit configured to receive a designation of a paper information piece to be associated with the sheet feeding unit among the list of paper information pieces belonging to the first group, and a unit configured to receive a designation of a paper information piece to be associated with the sheet feeding unit among the list of paper information pieces belonging to the second group.

Further features of the present invention will become apparent from the following description of embodiments with reference to the attached drawings.

BRIEF DESCRIPTION OF THE DRAWINGS

FIG. 6B illustrates a paper management flow.

FIG. 7B illustrates a registration screen for paper information piece.

FIG. 7C illustrates a screen for designating a paper information piece for a paper-feed stage.

FIGS. 9A to 9C illustrate screen transitions for registering a paper information piece with a paper-feed stage.

FIGS. 10A and 10B illustrate a screen transition for a favorite registration.

FIG. 12A illustrates a table of paper information pieces. FIG. 12B illustrates a table of paper-feed stage information pieces. FIG. 12C illustrates a table of information on favorite pieces.

FIG. 15 illustrates a flow of a favorite registration process.

FIGS. 16A to 16C illustrate screen transitions for a favorite registration.

DESCRIPTION OF THE EMBODIMENTS

Modes for embodying the present disclosure will be described with reference to drawings below.

Figure 1:
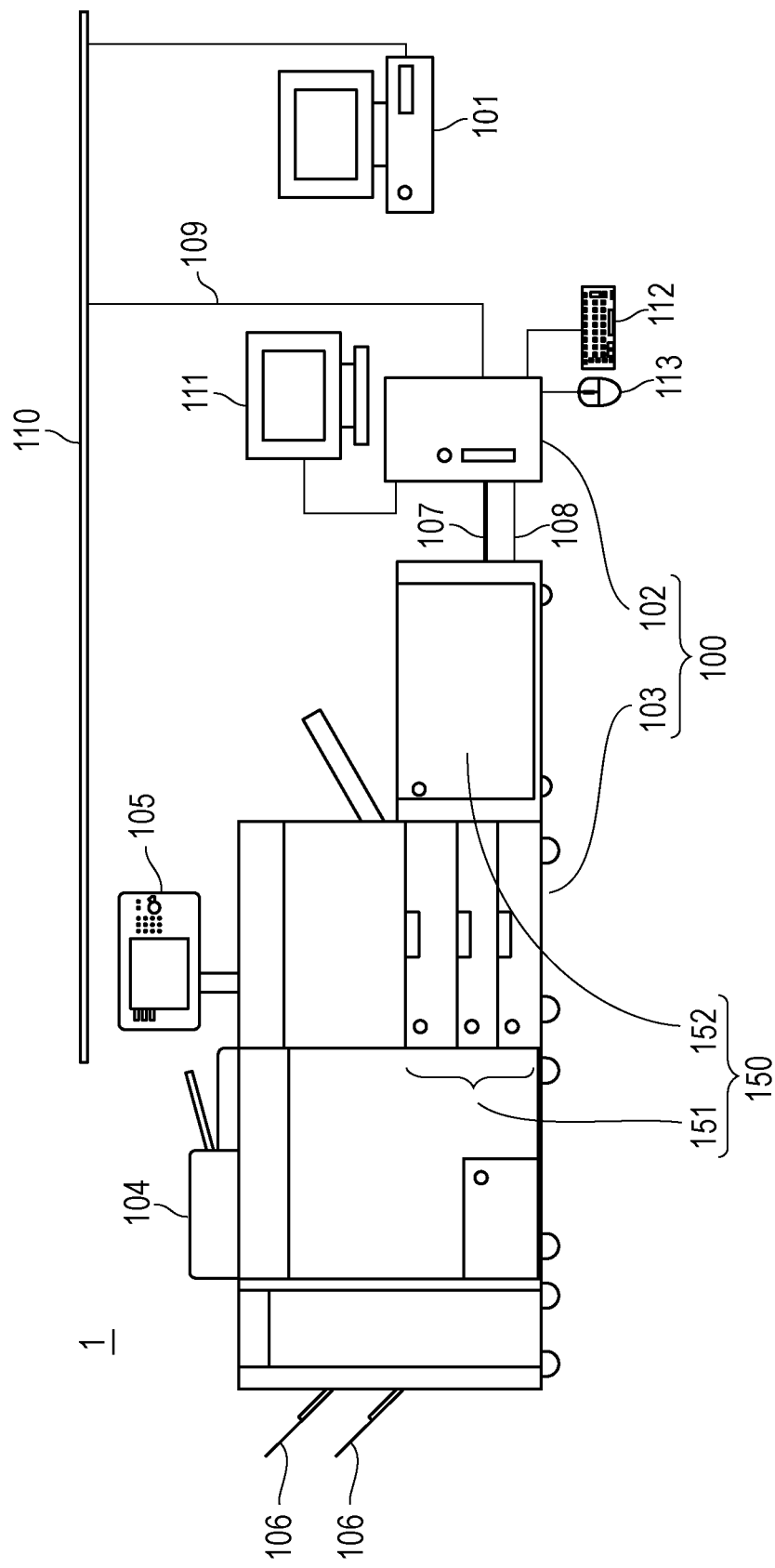
FIG. 1 illustrates an example of a configuration of a paper management system.

FIG. 1 illustrates an example of a configuration of a paper management system. A paper management system 100 in FIG. 1 includes an image forming apparatus 103 and a print control apparatus 102. The paper management system 100 is communicably connected with a client computer 101. The client computer 101 and the print control apparatus 102 are connected communicably over a local area network (LAN) 110 by using an Ethernet (registered trademark) cable 109. The print control apparatus 102 and the image forming apparatus 103 are connected via an image video cable 107 and a control cable 108. According to this embodiment, the image forming apparatus 103 is not directly connected with the LAN 110. The image forming apparatus 103 and the client computer 101 communicate through the print control apparatus 102. It should be noted that the image forming apparatus 103 may be connected with the LAN 110. In other words, the image forming apparatus 103 may directly and communicably be connected with the client computer 101.

The client computer 101 may transmit a print instruction to the paper management system 100 by starting up an application. The print control apparatus 102 may perform image processing in cooperation with the image forming apparatus 103. The image forming apparatus 103 may be a multi function peripheral having various functions and can perform image processing in cooperation with the client computer 101 or the print control apparatus 102, can copy data read by a scanner unit 104, and can send it to a shared folder. In a case where an image is to be scanned by the scanner unit 104, instructions can be received through a key on an operating unit 105. Also through the operating unit 105, information such as a scan state, can be displayed. A paper discharging unit 106 is configured to receive paper having an image thereon and to discharge the received sheet. The print control apparatus 102 has a display device 111 and may be an apparatus such as a liquid crystal monitor. A keyboard 112 and a pointing device 113 may also be provided.

Although, according to this embodiment, the paper management system 100 is described as a separate system from the print control apparatus 102 and the image forming apparatus 103. Processing to be performed by the print control apparatus 102 may be internally included in the image forming apparatus 103 so that the print control apparatus 102 may not physically be provided. The display device 111 may have a position input device function such as the one of a touch pad and may also be configured to have functionality of the pointing device 113.

Figure 2:
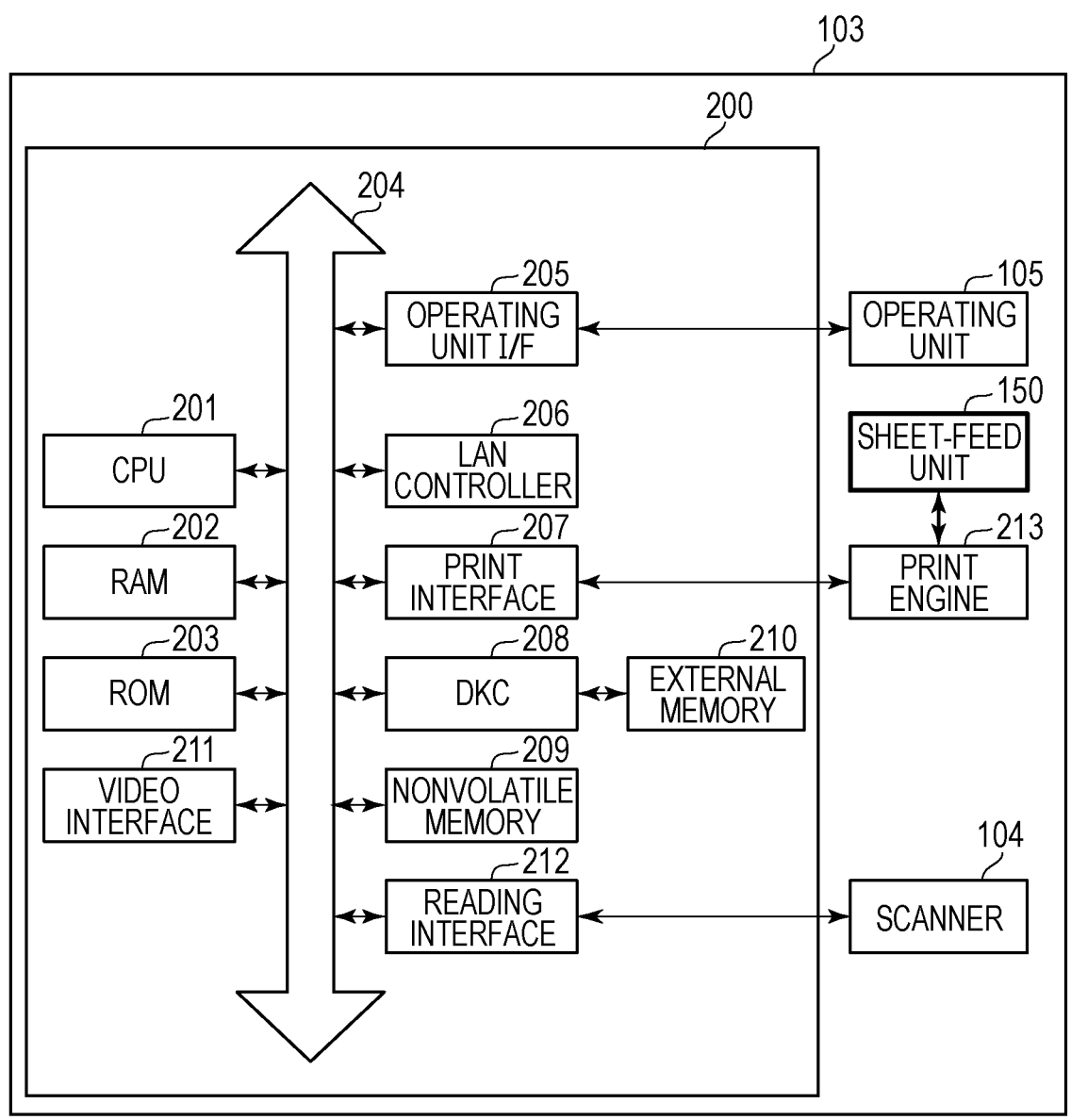
FIG. 2 illustrates a hardware configuration of an image forming apparatus.

FIG. 2 illustrates a hardware configuration of the image forming apparatus. FIG. 2 is a block diagram illustrating the image forming apparatus 103, and a controller 200 is configured to control the image forming apparatus 103 and includes from the CPU 201 to a reading interface 212. The CPU 201 is configured to generally control accesses to and from devices connected to a system bus 204 based on a control program stored in the ROM 203 or the external memory 210. The CPU 201 is further configured to output an image signal as output information to a printing unit (printer engine) 213 connected thereto through a print interface 207 and to control an image signal input from a reading unit (scanner) 104 connected thereto through the reading interface 212. The CPU 201 can perform communication processing with the print control apparatus 102 through a LAN controller 206. A RAM 202 mainly functions as a main memory or a work area for the CPU 201, for example. Accesses to the external memory 210 such as a hard disk (HDD) and an IC card may be controlled by a disk controller (DKC) 208. The hard disk may store an application program, font data, form data and so on and may be used as a job storage area for temporarily spooling a print job and externally controlling the spooled job. The hard disk may further hold image data read from the scanner 104 or image data from a print job as hold printing data, and may function as a hold printing data storage area to be referred or for printing over the network. According to this embodiment, an HDD is used as an external memory and is configured to hold logs such as a job log and an image log. An operation unit I/F 205 is configured to receive information input through the operating unit 105 (such as a software key or a hardware key) by a user and transmits a corresponding screen display control signal. A nonvolatile memory 209 is configured to store setting information defined by the operating unit 105 or a terminal over the network. A video interface 211 is configured to receive image data from the print control apparatus 102.

Figure 3A:
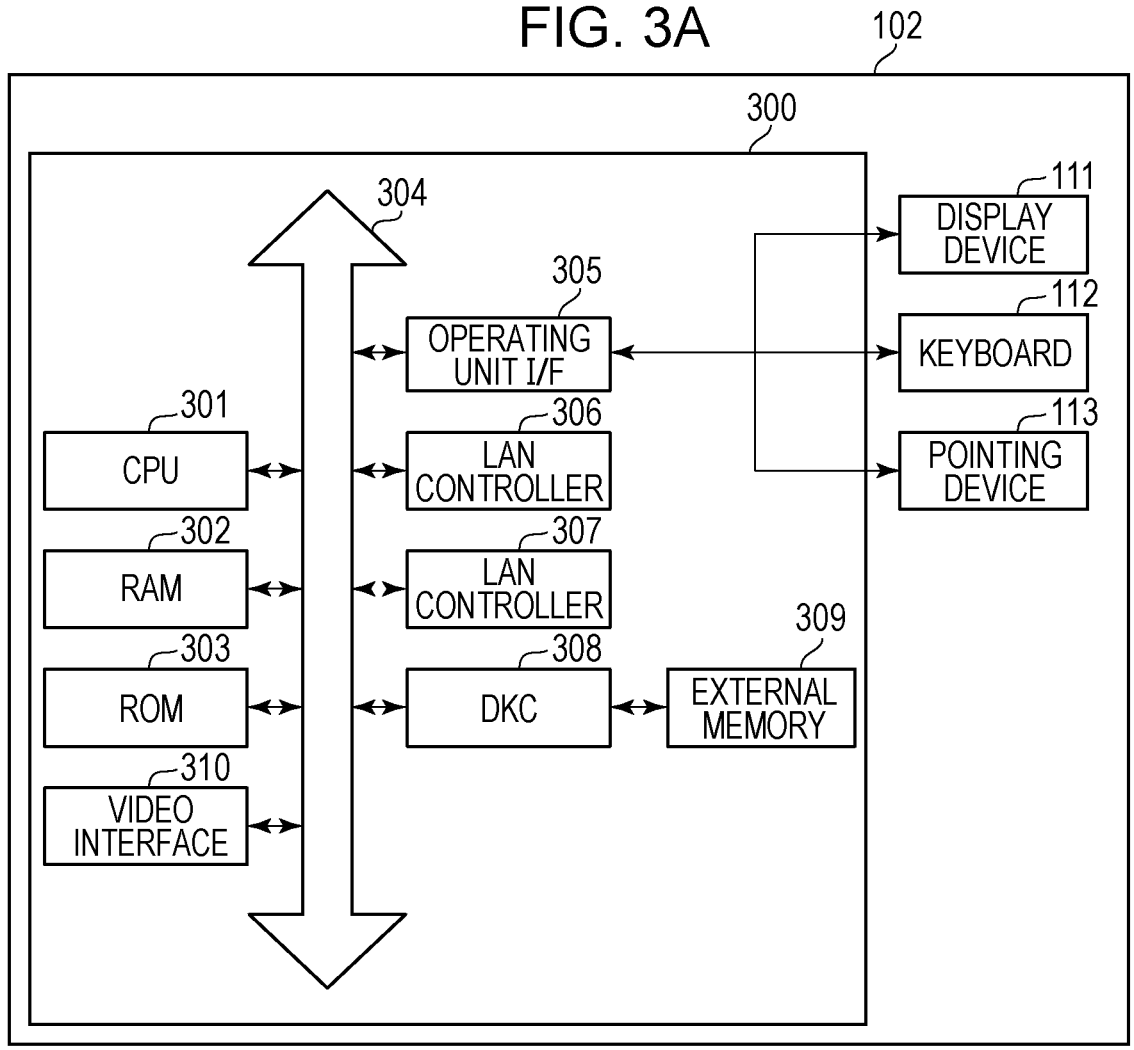
FIG. 3A illustrates a hardware configuration of a print control apparatus.

FIG. 3A illustrates a hardware configuration of the print control apparatus 102. Referring to the block diagram illustrating the print control apparatus 102 in FIGS. 3A and 3B, a controller 300 is configured to control the print control apparatus 102 and includes a CPU 301 to a video interface 310. The CPU 301 is configured to generally control accesses to devices connected to a system bus 304 based on a control program stored in a ROM 303 or an external memory 309. The CPU 301 is further capable of communication processing with the image forming apparatus 103 through a LAN controller 306. Through the LAN controller 307, the CPU 301 can perform communication processing with the client computer 101 and the image forming apparatus 103 over the network. A RAM 302 can mainly function as a main memory or a work area for the CPU 301. Accesses to an external memory 309 such as a hard disk (HDD) and an IC card are controlled by a disk controller (DKC) 308.

The hard disk may store an application program, a font data, form data and so on and is configured to temporarily spool print jobs. The hard disk may process spooled jobs in an RIP (Raster Image Processor) and may be used as a job storage area for storing them again. An operation unit I/F 305 is configured to receive information input from a user through the operating unit (such as keyboard 112 or pointing device 113) and to transmit a screen display control signal to the display device 111. The video interface 310 is configured to transmit the image data having undergone the RIP processing to the image forming apparatus 103.

Figure 3B:
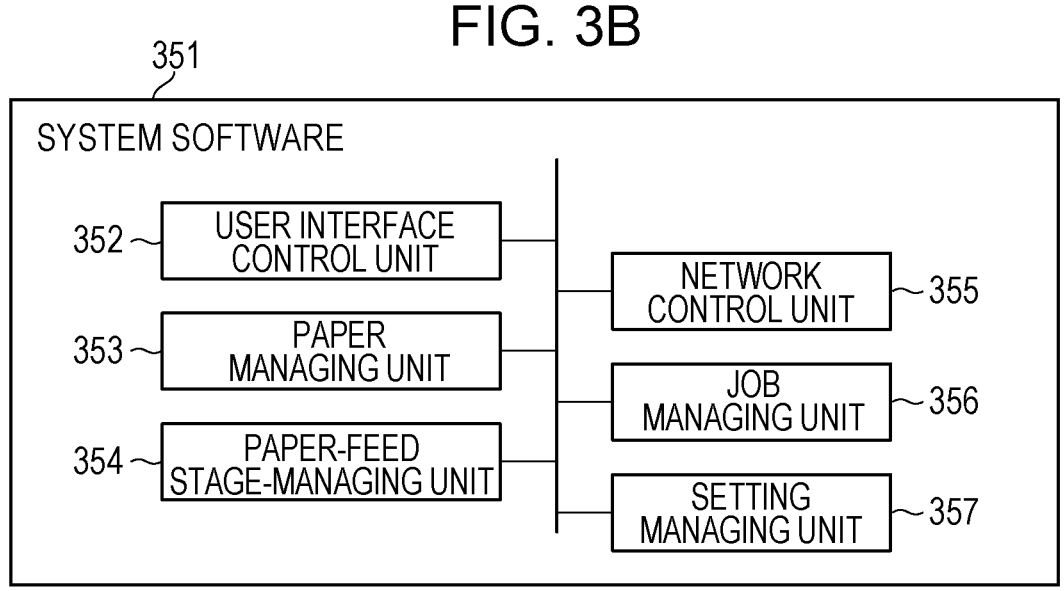
FIG. 3B illustrates a software configuration thereof.

FIG. 3B illustrates a software configuration thereof. System software 351 for controlling the print control apparatus 102 includes a user interface control unit 352, a paper managing unit 353, a paper-feed stage managing unit 354, a network control unit 355, a job managing unit 356, and a setting managing unit 357.

The user interface control unit 352 is configured to control a screen to be displayed on the paper management system. The user interface control unit 352 can control to change the display data on a display unit such as text to be displayed on a screen and a display unit system of a paper size based on system settings.

The paper managing unit 353 is configured to communicate with the image forming apparatus 103 to manage obtained paper information with reference to a paper setting management table 1210 in FIG. 12A. The paper managing unit 353 can edit, add, delete, and search paper information to or from the paper setting management table 1210. The paper setting management table 1210 is a management table for managing paper information for each paper ID and is managed in the external memory 309 that is a non-volatile storage area. Having described that the table is managed in the external memory 309, it may be managed in the external memory 210 on the image forming apparatus 103 side, and the print control apparatus 102 may obtain the paper setting management table 1210 from the image forming apparatus 103 and may be stored in the RAM 302 during execution of a program.

A paper-feed stage managing unit 354 communicates with the image forming apparatus 103 and is configured to manage obtained paper-feed stage information in a paper-feed stage management table 1220 in FIG. 12A. The paper-feed stage managing unit 354 can edit, add, delete, and search paper-feed stage information on the paper-feed stage management table 1220. The paper-feed stage management table 1220 is a management table for managing paper-feed stage information for each paper-feed stage ID and is managed in the external memory 309 that is a non-volatile storage area. Having described the table is managed in the external memory 309, it may be managed in the external memory 210 on the image forming apparatus 103 side, and the print control apparatus 102 may obtain the paper-feed management table 1220 from the image forming apparatus 103 and may be stored in the RAM 302 during execution of a program.

The network control unit 355 is configured to control processing for communicating with image forming apparatus 103 through the LAN controller 306 and the client computer 101 over the network through LAN controller 307.

The job managing unit 356 is configured to manage a print processing sequence or order of jobs. The job managing unit 356 is configured to manage a job received by the print control apparatus 102 and to control transfer of data for printing a received job to the image forming apparatus 103 through the LAN controller 306 and the video interface 310.

The setting managing unit 357 is configured to manage system settings regarding the paper management system and information on favorites (hereinafter, favorite information). The setting managing unit 357 is configured to manage favorite information on a favorite setting table 1230 in FIG. 12C. The setting managing unit 357 can edit, add, delete, and search information on favorite to or from the favorite setting table 1230. The system settings may include text to be displayed on a screen of the paper management system, language settings, and a display unit system for a paper size (millimeter or inch), for example. The setting table 1230 is a management table for managing setting information regarding the paper management system 100 and is managed in the external memory 309 that is a non-volatile storage area. Having described the table is managed in the external memory 309, it may be managed in the external memory 210 in the image forming apparatus 103 side, and the print control apparatus 102 may obtain the setting table 1230 from the image forming apparatus 103 and may be stored in the RAM 302 during execution of the program.

Figure 7A:
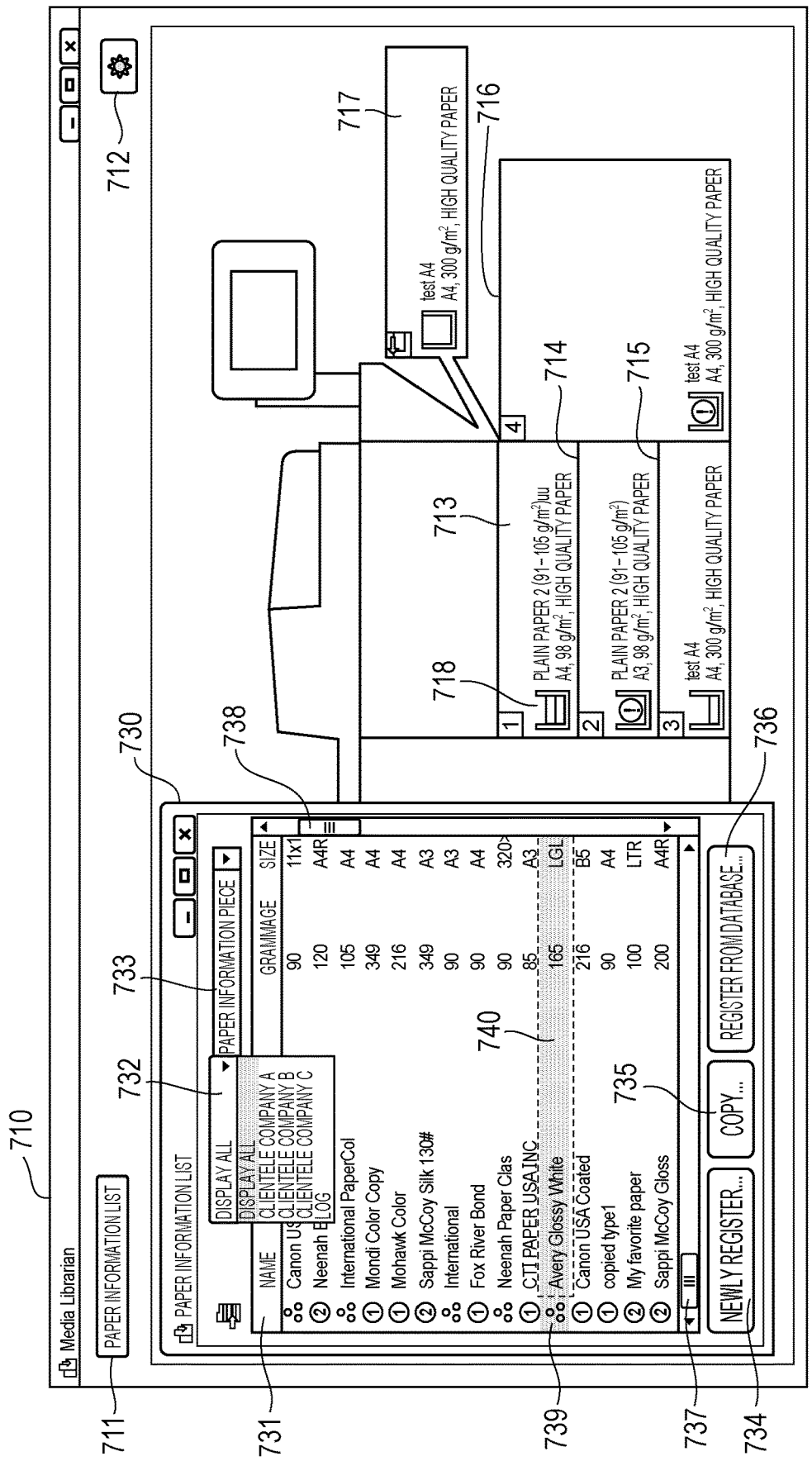
FIG. 7A illustrates a paper management screen.

FIG. 7A illustrates a paper management screen. FIG. 7B illustrates a paper information registration screen. FIG. 7C illustrates a screen for designating a paper for a paper-feed stage.

The paper management system runs on the print control apparatus 102. A top screen 710 in FIG. 7A displays information regarding paper-feed stages in the image forming apparatus 103. The top screen 710 according to the paper management system is stored as image data rendered in a video memory in response to an instruction from the CPU 301 and is output to the display device 111 as a video signal for display.

The top screen 710 is displayed as a top screen according to the paper management system and can display information on paper-feed stages in the image forming apparatus 103 (refer to FIG. 7A). The top screen 710 represents a connection state of a hardware option, which is connected with the print control apparatus 102, of the image forming apparatus 103. When the paper management system is started up, information regarding the hardware option in the image forming apparatus 103 is obtained, and a proper image is displayed based on the option information. Referring to FIGS. 7A, 7B and 7C according to this embodiment, five paper-feed devices (one of which is a manual feed tray), and a paper-discharging device is connected thereto. Paper-feed stage buttons 713 to 716 are provided. The paper-feed stage buttons are generated and are placed based on information regarding paper-feed stages (sheet feeding unit or storage unit) in the image forming apparatus 103, which is obtained upon start up of the paper management system. A paper remaining amount display unit 718 is an area configured to display a paper remaining amount of a paper-feed stage. The controller 300 obtains the paper-feed stage information again in response to an event that the state of a paper-feed stage has changed in the image forming apparatus 103, which is received from the image forming apparatus 103. The controller 300 re-renders the paper remaining amount display unit 718 based on the obtained paper-feed stage information.

A paper information list button 711 is a button for instructing to display a paper information list screen. According to this embodiment, if the button 711 is pressed, the controller 300 displays the paper information list screen 730 as in FIG. 7B and displays the paper information list screen 730 in the foreground.

Figure 4:
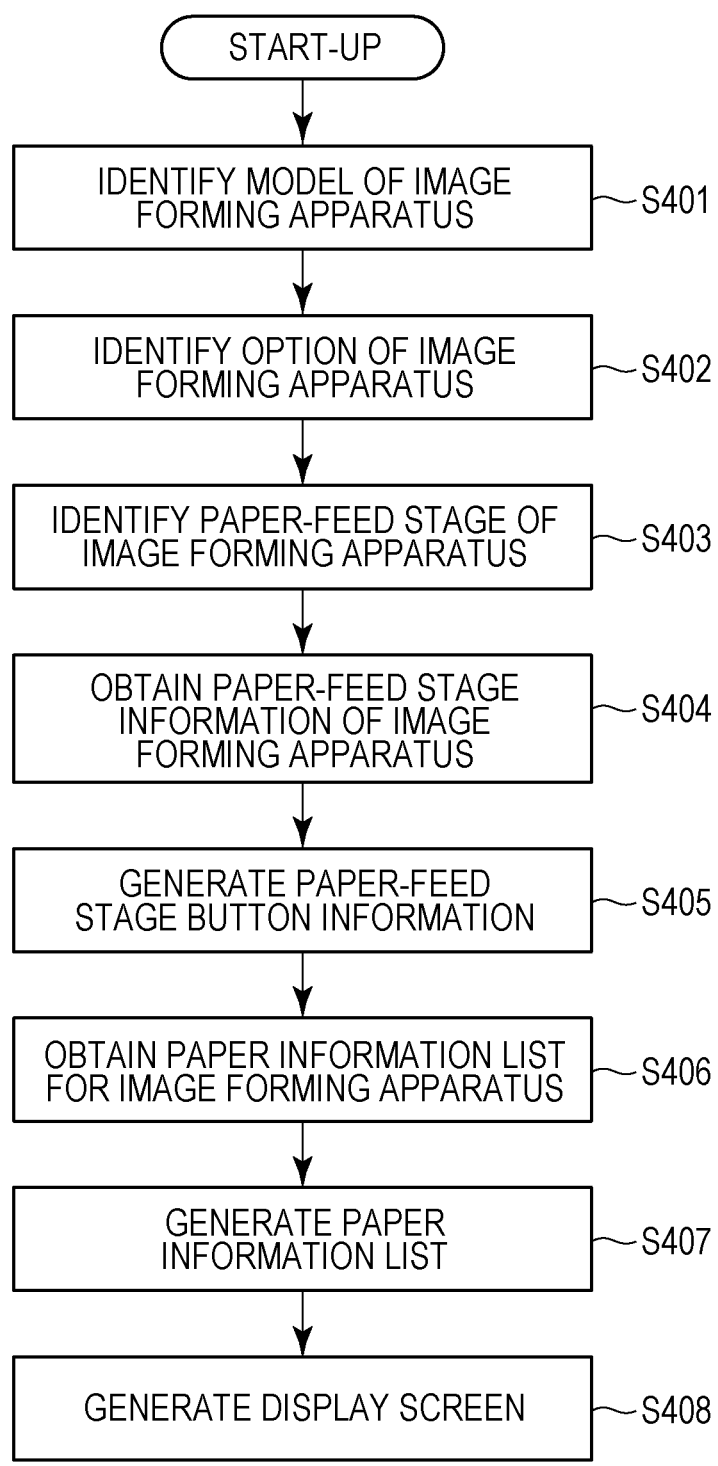
FIG. 4 illustrates a start-up flow for a paper management application.
Figure 5:
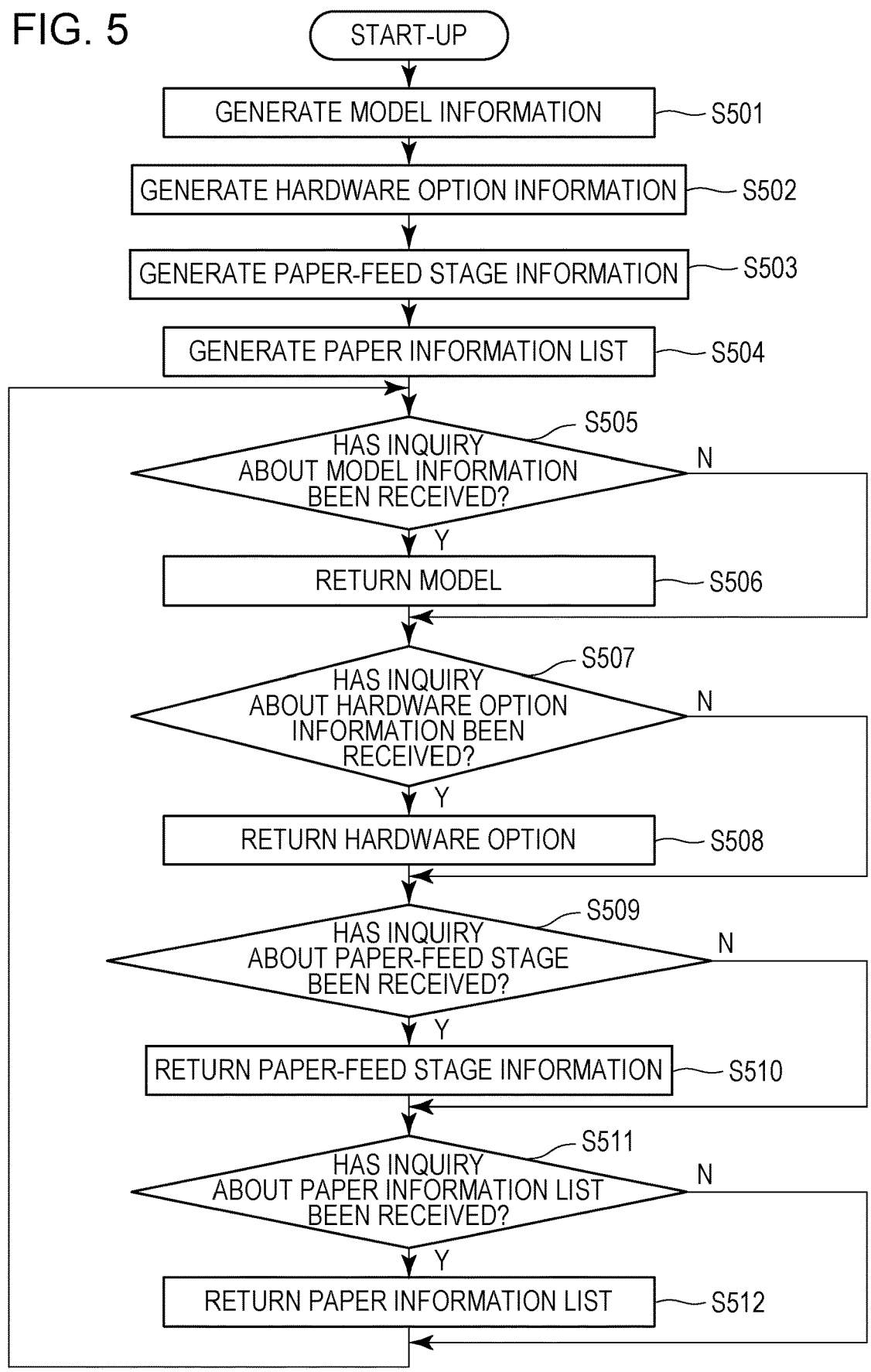
FIG. 5 illustrates a start-up flow for the image forming apparatus.

A setting button 712 is a button for instructing to display a screen for changing system settings for the paper management system. The controller 300 is configured to display current system settings based on the system settings stored in the external memory 309. FIG. 4 is a flowchart of processing to be performed by the print control apparatus 102 configured to process when the top screen 710 is generated upon start up of the paper management system. FIG. 5 illustrates a start-up flow of the image forming apparatus. As illustrated in FIG. 5, the image forming apparatus 103 generates information to be synchronized with the print control apparatus 102 by communicating with the print control apparatus 102 upon start up.

FIG. 4 illustrates a start-up flow of a paper management application.

A program in the print control apparatus 102 according to the flowchart in FIG. 4 is stored in the external memory 309 in FIG. 3A, is read out to the RAM 302, and is executed by the CPU 301. Upon start up of the paper management system, the controller 300 in S401 identifies the model of the image forming apparatus 103 to be paper-managed. The controller 300 communicates with the image forming apparatus 103 to obtain the model information and identifies the model of the image forming apparatus 103 based on model identification information pre-held in the paper management system.

If the model is identified in S401, the processing moves to S402.

In S402, the controller 300 identifies a hardware option connected to the image forming apparatus 103, and when the top screen 710 is generated, the model identification information is used for identifying paper-feed stage information or when a difference in specifications between models is absorbed. If the hardware option information is obtained through the communication with the image forming apparatus 103, the processing moves to S403.

In S403, the controller 300 identifies a paper-feed stage connected to the image forming apparatus 103 to be paper-managed. The number of paper-feed stages connected thereto and paper-feed stage information are obtained. For example, the paper-feed stage information obtained here may include a paper-feed stage name, a paper-feed stage ID, and the sheet remaining amount of the paper-feed stage. If a paper-feed stage is identified in S403, the controller 300 controls the paper-feed stage managing unit 354 to write the obtained paper-feed stage information to the paper-feed stage management table 1220. The processing moves to S404.

In S404, the controller 300 obtains paper information regarding paper set in the paper-feed stage by communicating with the image forming apparatus 103. If the paper information (such as a paper ID) regarding the paper-feed stage is obtained in S404, the controller 300 controls the paper-feed stage managing unit 354 to write the obtained paper ID to an area matched with the corresponding paper-feed stage ID on the paper-feed stage management table 1220. Then, the processing moves to S405.

In S405, the controller 300 generates information (paper-feed stage information) on paper-feed stage buttons 713 to 717 to be displayed on the top screen 710. If information of the paper-feed stage buttons is generated in S405, the processing moves to S406.

In S406, the controller 300 obtains a paper information list by communicating with the image forming apparatus 103. The paper information may include, for example, a paper name, parameters for printing (such as a grammage and a size of a paper to be displayed on an paper information input area 751, set values for adjustment of glossiness/black quality to be displayed on an adjustment item list 754), favorite IDs, usage logs, settable paper-feed stage IDs. If the paper information list is obtained in S406, the controller 300 controls the paper managing unit 353 to write the obtained paper information to the paper setting management table 1210. Then, the processing moves to S407. In S407, the controller 300 generates a paper information list to be displayed on a paper information list display area 731 of the paper information list screen 730. In the print control apparatus 102, the controller 300 can control the paper managing unit 353 to determine whether a paper-feed stage ID is settable for a paper-feed stage based on the obtained paper information or not. Alternatively, the controller 300 may control the paper managing unit 353 to inquire about whether the paper information obtained for the image forming apparatus 103 is settable for a paper-feed stage, and a settable paper-feed stage ID returned from the image forming apparatus 103 may be set. A usage log is information indicating the number of times of allocation of a paper information piece, and is set at zero when a paper information piece is created and increments when the paper information piece is allocated to a certain paper-feed stage.

If the controller 300 generates the paper information list in S407, the processing moves to S408.

In S408, the controller 300 generates a top screen 710 based on the model hardware option information on the image forming apparatus 103 obtained in S401 and S402 and the paper-feed stage information generated in S405. The controller 300 generates a paper information list screen 730 based on the paper information list generated in S407. A display device 111 with a lower resolution may have a narrow screen display area. Therefore, the paper information list screen 730 may sometimes be displayed over the top screen 710. In a case where the paper information list screen 730 is closed and the paper management system is then re-started, the top screen 710 may only be displayed upon next start-up. In this case, an operator may press a paper information list button 711 on a top screen after the start-up so that the paper information list screen 730 may display in accordance with the information obtained in steps S405 and S407.

FIG. 5 illustrates a start-up flow of the image forming apparatus. A program for the image forming apparatus 103 according to the flowchart in FIG. 5 is stored in the external memory 210 in FIG. 2, be read out to the RAM 202 and be executed by the CPU 201. The image forming apparatus 103 upon start-up moves to S501. In S501, the controller 200 obtains model information of the controller 200 itself from the external memory 210 and generates it as returnable data.

If the data of the model information is generated in S501, the processing moves to S502.

In S502, the controller 200 obtains information on a hardware option connected thereto from the print engine 213 through the print interface 207 and generates it as a returnable data to the RAM 202. If the data of the hardware option information is generated in S502, the processing moves to S503.

In S503, the controller 200 obtains information regarding a hardware option from which the corresponding paper-feed stage information is obtained from the RAM 202 and generates it as a returnable data. If the data of the paper-feed stage information is generated in S503, the processing moves to S504.

In S504, the controller 200 obtains paper information list of the controller 200 itself from the external memory 210 and generates as returnable data. If the data of the paper information list is generated in S504, the processing moves to S505.

In S505, the controller 200 determines whether inquiry about model information has been received from the print control apparatus 102. If the inquiry about the model information has been received, the processing moves to S506 where the model information generated in S501 is returned. The processing moves to S507. If not, the processing also moves to S508.

In S507, the controller 200 determines whether the inquiry about the hardware option information has been received from the print control apparatus 102. If the inquiry about the hardware option information has been received, the processing moves to S508 where the hardware option information generated in S502 is returned, and the processing moves to S509. If not in S507, the processing also moves to S509.

In S509, the controller 200 determines whether an inquiry about the paper-feed stage information has been received from the print control apparatus 102. If the inquiry about the paper-feed stage information has been received, the processing moves to S510 where the paper-feed stage information generated in S503 is returned. The processing moves to S511. If the inquiry about the paper-feed stage information has not been received in S509, the processing also moves to S511.

In S511, the controller 200 determines whether an inquiry about the paper information list has been received from the print control apparatus 102. If the inquiry about the paper information list has been received, the processing moves to S512 where paper information list generated in S504 is returned. The processing moves to S505. If not in S511, the processing also moves to S505.

Referring back to FIGS. 7A, 7B and 7C, when a button 713 on a paper-feed stage 1 is pressed by using, for example, the pointing device 113, a paper settings screen 770 for the paper-feed stage 1 as in FIG. 7C is displayed. Because buttons 714 to 717 are similar to the button 713, any repetitive descriptions will be omitted. The term "paper-feed stage" refers to one including all of paper feeders such as an inserter and a manual feed tray, details of which will not be described according to this embodiment. Although it is apparent that an input device is used for operations, use of the pointing device 113, for example, when an application operates in response to a press of the button will not describe below.

FIG. 7C illustrates the paper settings screen 770 for the paper-feed stage 1. The paper settings screen 770 is rendered in a corresponding video memory in response to an instruction from the CPU 301, and the image data rendered in the video memory is output to and displayed on the display device 111 as a video signal. The paper settings screen 770 displays a paper information list display area 771, a paper information display area 772, a button 773 for displaying an adjustment screen for an adjustment item, a button 774 for displaying a setting screen for other paper information that is not displayed there, an OK button 775, and a cancel button 776. Because the paper information list display area 771 displays the same information as the area 731 of the paper information list screen 730, any detail repetitive descriptions will be omitted. While the paper settings screen 770 is being displayed, paper set in the present paper-feed stage is selected on the paper information list display area 771. If paper is selected from the paper information list 771, the paper information display area 772 displays information regarding the selected paper. If another paper is selected on the paper information list display area 771 and the OK button 775 is pressed, the controller 300 defines paper settings for the image forming apparatus 103. If another paper is selected on the paper information list display area 771 and the cancel button 776 is pressed, the controller 300 does not define paper settings for the image forming apparatus 103, and the paper settings screen 770 is closed. The paper information display area 772 displays setting information on the currently selected paper. If the paper-feed stage button 713 on the top screen 710 in FIG. 7A is pressed and the screen 770 is opened, information regarding the paper currently allocated to the paper-feed stage 1 is displayed.

Items of the paper information display area 772 will be described. For improved convenience of an operator, only paper information frequently used by the operator is displayed as an example according to this embodiment. More specifically, the information includes a paper name and adjustment items (image position adjustment, secondary transfer voltage adjustment, curl correction amount, glossiness/black quality adjustment, correction of white void at back end, saddle stitch setting, air flow adjustment for sheet fan. Because these items will be described in descriptions about the paper setting screen 750 in FIG. 7B, they are not described here. The paper information display area 772 displays a name of the currently selected paper and whether the adjustment values have been changed from initial values for the image forming apparatus 103 or not. If they are not changed, "NOT ADJUSTED" is displayed. If they are changed, "ADJUSTED" is displayed. A button 773 is displayed for an item which can be adjusted from the print control apparatus 102, and it is configured to be capable of displaying corresponding adjustment screen.

The button 774 is a button to be pressed to check information displayed in the paper information display area 772 or to define settings. For example, it may be configured to display a paper setting screen 750 in FIG. 7B.

Although a paper management application runs on the print control apparatus 102 according to this embodiment, embodiments of the present disclosure are not limited by such a paper management application. The same mechanism may be implemented in the client computer 101 or the image forming apparatus 103.

Embodiment 1

Figure 6A:
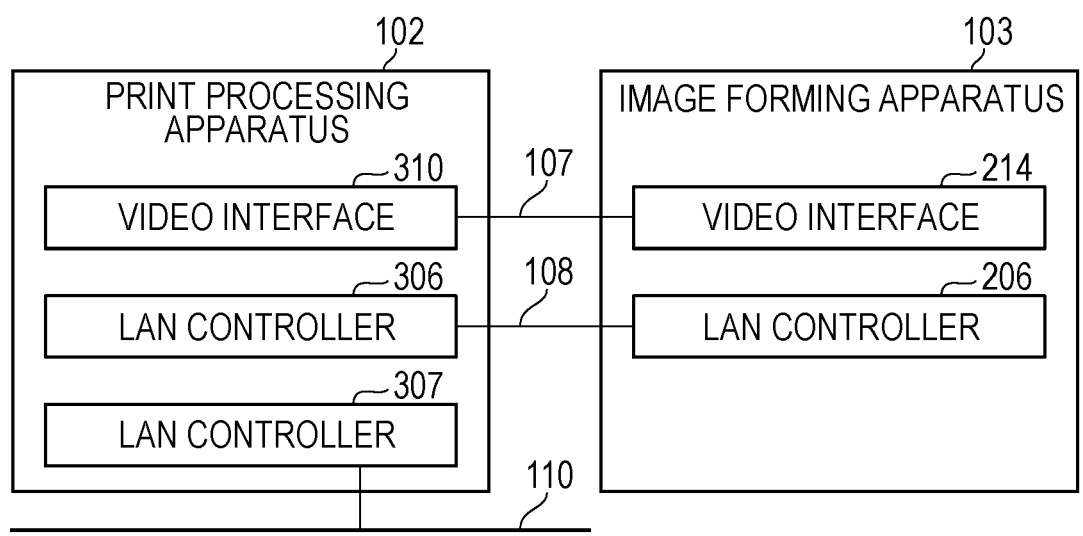
FIG. 6A illustrates a communication configuration of the paper management system.

Processing to be performed by the print control apparatus 102 and the image forming apparatus 103 according to Embodiment 1 will be described with reference to FIGS. 6A and 6B. FIG. 6A illustrates a communication configuration of the paper management system. FIG. 6B illustrates a paper management flow. A program in the print control apparatus 102 which will be described below is stored in the external memory 309 in FIG. 3A so that it can be read out to the RAM 302 and can be executed by the CPU 301.

According to this embodiment, an operator is enabled to use a plurality of favorite settings for frequently used paper information pieces. Information on a favorite included in the paper information can be used prior to printing to find a desired paper information piece and define paper settings for printing. The term "favorite" in this embodiment is identification information by which an operator can easily find his or her desired paper information piece. According to this embodiment, a favorite ID is provided as one paper information piece as an example. Assume a case where there may be an order for additional 100 copies of print materials that have been printed once in a printing factory. In this case, because the same paper information piece as that of the last printing is to be used, the paper information piece may be defined as a favorite so that it can be found out as a paper information piece that is frequently additionally ordered by a customer. More specifically, for customers who frequently additionally order, for example, favorites labeled as "Clientele Company A", "Clientele Company B", and "Clientele Company C", and may be defined for a paper information piece to be used by each of the customers. When there is a plurality of customers, one favorite is not useful for distinguishing between them. Therefore, a plurality of favorite IDs may be provided as paper information pieces.

Next, with reference to the flow in FIG. 6B, a flow will be described in which a printing factory receives a print order for a house leaflet (with paper of Mohawa Color) from Clientele Company A, causing an operator to print the house leaflet. It is assumed here the printing factory can distinguish the paper to be used by the clientele is based on the favorite type from other paper information pieces. It is also assumed that Clientele Company A, Clientele Company B, and Clientele Company C are registered as favorites, and a corresponding paper information piece has been registered for each clientele.

Favorite Managing Unit

Figure 8A:
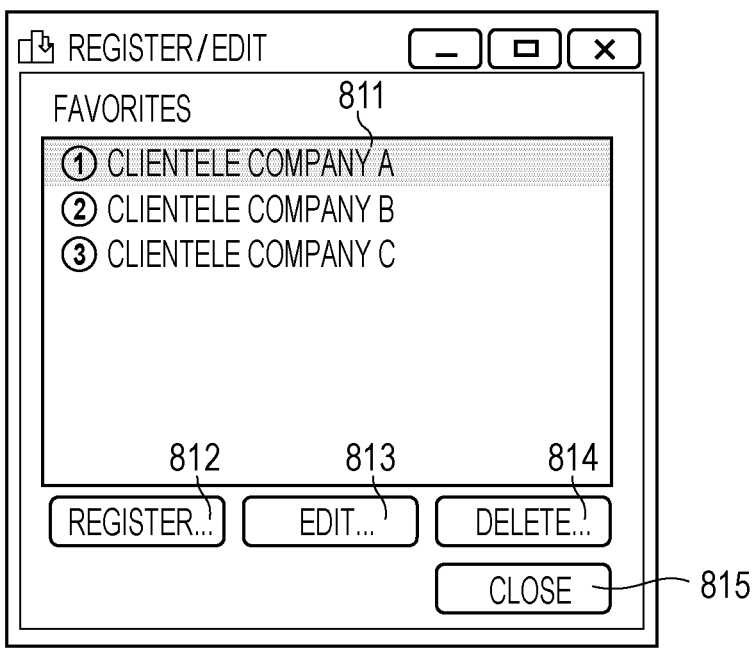
FIG. 8A illustrates a screen for editing a favorite group.
Figure 8B:
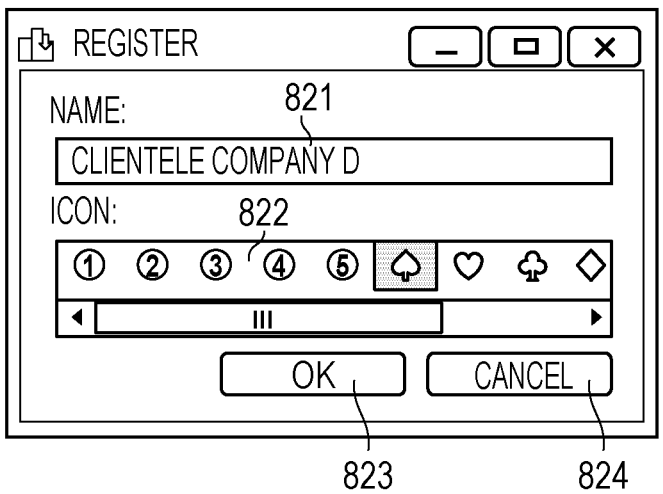
FIG. 8B illustrates a screen for editing a favorite group.
Figure 8C:
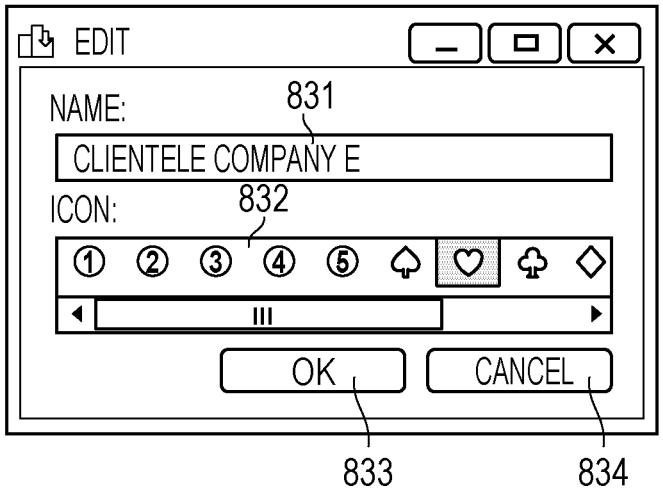
FIG. 8C illustrates a screen for editing a favorite group.

First, a favorite managing unit will be described with reference to FIGS. 8A, 8B and 8C and FIGS. 11A and 11B. FIG. 8A illustrates a screen for editing a favorite group. FIG. 8B illustrates a screen for editing a favorite group. FIG. 8C illustrates a screen for editing a favorite group. According to this embodiment, a favorite management screen 810 in FIG. 8A corresponds to a managing unit for favorites. The favorite management screen 810 is displayed in response to a press of a favorite register/edit button 753 on the paper setting screen 750. It may be configured to shift from a setting screen displayed in response to a press of a setting button 712 on the top screen 710 to the favorite management screen 810.

The favorite management screen 810 in FIG. 8A includes a favorite list 811, a register button 812, an edit button 813, a delete button 814, and close button 815.

The favorite list 811 is configured to display a list of names of favorites registered with a favorite setting table 1230 corresponding to a paper management system. The controller 300 controls the user interface control unit 352 to obtain the name of favorite, the favorite ID, the icon ID in the favorite setting table 1230 from the setting managing unit 357 to generate the favorite management screen 810. For example, the management screen 810 vertically displays icon images corresponding to icon IDs and names of favorites based on the favorite setting table 1230. On a favorite list 811, the currently selected favorite has a selected state.

FIG. 12A illustrates a table of paper information. FIG. 12B illustrates a table of paper-feed stage information. FIG. 12C illustrates a table of information on favorites.

Next, the favorite setting tables 1230 in FIGS. 12A, 12B and 12C will be described. A favorite setting table is a setting table for storing categories of favorites in the paper management system. The favorite setting table 1230 is managed by the setting managing unit 357 and is configured to be stored in the external memory 309 that is a nonvolatile area. The favorite setting table 1230 includes names of favorites, favorite IDs, and icon IDs. Each of the names of favorites is a name for presentation to a user on a screen. Each of the favorite IDs is identification information by which a favorite can be distinguished. Each of the icon IDs is an ID by which an icon can be identified and allows distinction of favorites along with a list of paper information list names on, for example, the paper information list screen 730. It is assumed here that a distinguishable icon ID is pre-assigned to an icon displayed on icon lists 822 and 833, which will be described below. For example, icon IDs are assigned serially in order from left to right of the icons such as a "1" within a circle indicating an icon ID=1, "2" within a circle indicating an icon ID=2. The controller 300 controls user interface control unit 352 to read an icon corresponding to an icon ID and display the icon on the screen.

A button 812 is for newly registering a favorite. If the button 812 is pressed, the controller 300 controls the user interface control unit 352 to display a favorite registration screen 820.

A button 813 is for editing a favorite selected on the favorite list 811. If the button 813 is pressed, the controller 300 controls the user interface control unit 352 to display a favorite edit screen 830.

A button 814 is for deleting a favorite selected on the favorite list 811. If the button 814 is pressed, the controller 300 controls the setting managing unit 357 to delete a selected favorite.

A button 815 is for closing the favorite management screen 810. If the button 815 is pressed, the controller 300 controls the user interface control unit 352 to close the favorite management screen 810.

Next, a favorite registration screen 820 in FIG. 8B will be described. The favorite registration screen 820 includes a name input field 821, an icon list 822, an OK button 823, and a cancel button 824. The name input field 821 is a text field in which a name of a favorite can be input. In order to change the name, text can be input to the text area by using, for example, the keyboard 112. Any kind of input device such as the keyboard 112 can be used to input text although a case where the keyboard 112 is used for input will not be described below. If the OK button 823 is pressed, the controller 300 controls the setting managing unit 357 to add the input name and an icon ID of the selected icon to the favorite setting table 1230. If the cancel button 824 is pressed, the controller 300 controls the user interface control unit 352 to close the favorite registration screen 820. The icon list 822 is an icon list which can be displayed in the paper information list display area 731 on the paper information list screen 730 or in the favorite setting area 752 on the paper setting screen 750. An operator can select one icon to be used from the icon list.

Next, the favorite edit screen 830 in FIG. 8C will be described. The favorite edit screen 830 includes a name input field 831, an icon list 832, an OK button 833, and a cancel button 834. Because the name input field 831 is similar to the name input field 821, any repetitive description will be omitted. Because the icon list 832 is also similar to the icon list 822, any repetitive description will be omitted. If the OK button 833 is pressed, the controller 300 controls the setting managing unit 357 to write the changed name and the icon ID of the selected icon in the favorite area corresponding to the selected favorite ID selection in a setting table 1230. Because the cancel button 834 is similar to the cancel button 824, any repetitive description will be omitted.

Figure 11A:
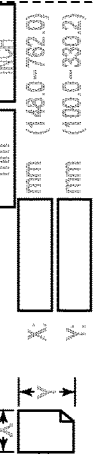
FIGS. 11A and 11B illustrate screen transitions for editing a favorite group.
Figure 11B:
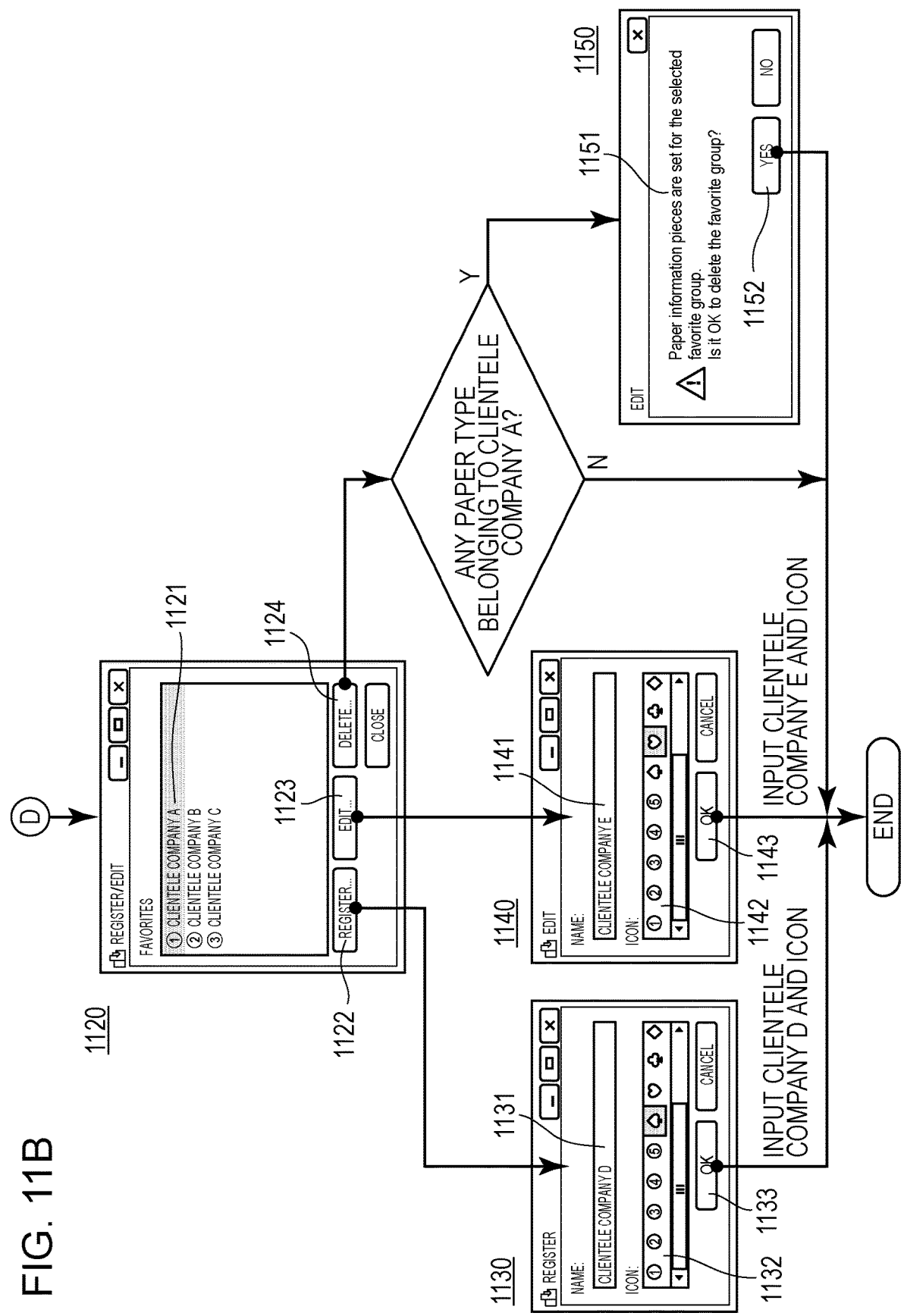

Next, screen transitions among the screens illustrated in FIGS. 8A, 8B and 8C will be described with reference to FIGS. 11A and 11B. FIGS. 11A and 11B illustrate screen transitions for editing a favorite group. First, a screen transition for new registration of a favorite will be described. If a favorite register/edit button 1111 in FIG. 11A on a screen 1110 (corresponding to the paper setting screen 750) is pressed, the controller 300 controls the user interface control unit 352 to display a screen 1120 (corresponding to the favorite management screen 810). If a register button 1122 is pressed on the screen 1120, the controller 300 controls the user interface control unit 352 to display a screen 1130 (corresponding to the favorite registration screen 820). If "Clientele Company D" in a name input field 1131 and "spade" in an icon list 1132 on the screen 1130 are selected and a button 1133 is pressed, the controller 300 adds an input information to the favorite setting table 1230. More specifically, the controller 300 controls the setting managing unit 357 to write "Clientele Company D" as the name of favorite, 4 (because 1 to 3 have already been used up to this point) as a favorite ID, and 6 as an icon ID. The controller 300 controls the user interface control unit 352 to close the screen 1130.

Next, screen transitions for editing a registered favorite will be described. If, on the screen 1120, "Clientele Company A" is selected in the favorite list 1121 and the edit button 1123 is pressed, the controller 300 controls the user interface control unit 352 to display a screen 1140 (corresponding to the favorite edit screen 830). If, on the screen 1140, "Clientele Company E" is selected in a name input field 1141, "heart" is selected in an icon list 1142, and a button 1143 is pressed, the controller 300 overwrites the input information in the favorite setting table 1230. More specifically, the controller 300 controls the setting managing unit 357 to write "Clientele Company E" as a name of favorite and 7 as an icon ID in a favorite ID=1 area. The controller 300 controls the user interface control unit 352 to close the screen 1130.

Finally, screen transitions for deleting a registered favorite will be described. If, on the screen 1120, "Clientele Company A" is selected in the favorite list 1121 and the delete button 1124 is pressed, the controller 300 controls the paper managing unit 353 to search whether any paper has the selected favorite ID. The paper managing unit 353 obtains all of registered paper information pieces and compares the IDs of the paper information pieces of paper with the favorite ID to detect a match. If it is detected that there is a paper belonging to favorite ID=1 of Clientele Company A, the controller 300 aborts the search and controls the user interface control unit 352 to display a warning screen 1150. The warning screen 1150 is to be displayed to confirm whether a paper information piece having the applicable favorite ID if any is to be deleted or not. The warning screen 1150 displays an icon and words for warning in a message area 1151. If a "YES" button 1152 is pressed, the controller 300 controls the setting managing unit 357 to delete settings for the row of the favorite ID=1 (Clientele Company A) from the setting table 1230. The controller 300 controls the paper managing unit 353 to delete favorite ID=1 from the favorite ID of the paper information pieces for all paper information pieces in the paper setting management table 1210. For example, favorite IDs of a paper type (Mohawk Color) having the paper ID=1 in the paper setting management table 1210 are overwritten with 2, 3, 4. The controller 300 controls the user interface control unit 352 to re-render the screen 1110 and the paper information list screen 730 that are being displayed. In a case where the favorite to be deleted is not set in any paper information pieces, the controller 300 controls the setting managing unit 357 to delete the sets of the row having favorite ID=1 (Clientele Company A) from the setting table 1230. The controller 300 controls the user interface control unit 352 to re-render the screen 1110 and the paper information list screen 730 that are currently being displayed. Up to this point, the managing unit for a favorite has been described.

Favorite Setting Unit

Next, a favorite setting unit will be described. According to this embodiment, a favorite registering unit includes two execution units configured to set the paper setting screen 750 in FIG. 7B and configured to perform a defining operation by right-clicking on the paper information list screen 730 illustrated in FIG. 7A.

The unit for performing a defining operation on the paper setting screen 750 in FIG. 7B will be described. The paper setting screen 750 is a screen for newly registering a paper information piece and editing a registered paper information piece. The paper setting screen 750 includes a paper information input area 751, a paper information adjustment item list 754, a pull-down menu 755 for changing the displayed group of adjustment item lists, an OK button 756, and a cancel button 757.

The paper information input area 751 displays minimum setting items for handling a paper within the paper information. According to this embodiment, for example, the setting items to be displayed may include a name, a grammage, a color, a surface property, a size, a feature, double-sided/second surface, and favorites. Because this description focuses on favorites, the other setting items than favorites will be described only briefly. An object 761 is a text area in which a name of a paper can be input. In order to change the name, text can be input by using the keyboard 112 in the text area. For example, the text area may be blank for new registration and may display the name of the currently selected paper for editing. In order to reflect the changed information to the paper information, the OK button 756 on the paper setting screen 750 may be pressed. If the OK button 756 is pressed, the paper information regarding the print control apparatus 102 and the image forming apparatus 103 can be changed.

The OK button 756 on the paper setting screen 750 is pressed. If the cancel button 757 is pressed, a paper setting can be cancelled. An object 762 is a text area in which a grammage can be input. Because operations to be performed thereon are equivalent to those to be performed on the name text area being the object 761, any repetitive descriptions will be omitted. An object 763 is a pull-down menu displaying color information of a paper which can be selected from the list. An object 764 is a pull-down menu displaying a surface property information, which can be selected from the list. An object 765 is a pull-down menu list displaying size information of a sheet, which can be selected from the list. An object 766 is a text area in which lengths in main-scanning and sub-scanning directions of a sheet size, which can be input when a user defined size is selected in the object 765. The paper setting screen 750 is gray-out to prevent inputting because the sheet size is A4. The input units may include a button or buttons for switching between millimeter and inch. An object 767 is a pull-down menu list displaying characteristic information which can be selected from the list. An object 768 is a pull-down menu list displaying a flap position of an envelope, which can be selected from the list. The object 768 is a pull-down menu list which accepts an input if an envelope is selected in the object 767. An object 769 is a radio button displaying a double-sided/second surface information to switch between "set" and "not set". The double-sided/second surface information is a setting for changing voltage of the transfer in a case where a sheet having a front side fixed is put to the corresponding paper-feed stage to fix its back side.

A favorite setting area 752 is a menu displaying a favorite list stored in the favorite setting table 1230, in which a favorite to which the settings belongs can be set. Here, when the favorite list 752 is displayed along with check boxes, and if a checkbox is checked, it indicates that the setting belongs to a target favorite. For example, in the object 752, because three favorites (Clientele Company A, Clientele Company B, Clientele Company C) are not checked, it means that the settings do not belong to any of favorites. In order to reflect the changed information to the paper information, the OK button 756 on the paper setting screen 750 may be pressed. If the OK button 756 is pressed, the paper information for the print control apparatus 102 and the image forming apparatus 103 can be changed. In response to an instruction to generate a paper setting screen 750, the controller 300 controls the setting managing unit 357 to obtain the favorite setting table 1230. The controller 300 controls the user interface control unit 352 to display the paper setting screen 750 based on the information on the obtained favorite setting table 1230.

The favorite register/edit button 753 is for displaying a favorite management screen 810. Because the favorite management screen 810 has already been described, any repetitive description will be omitted.

The adjustment item list 754 displays a name, the necessity of adjustment, and a list of a display group for items which can be adjusted with a set value included in the paper information. For determination of the necessity of adjustment of an adjustment item, if an adjustment item is selected in the object 754, a detail value of an adjustment value and an adjustment button are displayed on the paper setting screen 750 so that a target adjustment screen can be displayed in response to a press of the adjustment button. Adjustment items displayed in the object 754 will be described briefly. "Glossiness/black quality adjustment" is an item for adjusting the temperature of a fixing unit when plain paper or coated paper is used to adjust the glossiness of an output image. This is defined to belong to a display group "quality". "Adjustment of secondary transfer voltage" is an adjustment item for changing voltage to transfer a toner image to a sheet. This is defined to belong to a display group "quality". "White void correction at back end" is an adjustment item for changing the transfer voltage when toner is removed to white or to be light at a trailing end of a sheet in the conveying direction. This is defined to belong to a display group "quality". "Adjustment of secondary transfer antistatic bias" is an adjustment item for change the voltage value (antistatic bias) to remove static electricity remaining in an intermediate transfer belt. This is defined to belong to a display group "quality". "ITB image removal adjustment" is an adjustment item for changing the degree of image removal of an intermediate transfer belt. This is defined to belong to a display group "quality". "Toner amount adjustment mode" is an adjustment item for changing a total amount of toner. This is defined to belong to a display group "quality". "Adjustment of primary transfer voltage" is an adjustment item for changing voltage to transfer a toner image from an intermediate transfer belt to a sheet. This is defined to belong to a display group "quality".

"Adjustment of registration loop amount" is an adjustment item for changing the amount of bending of a sheet which is formed when an image position is being adjusted. This is defined to belong to a display group "quality". "Adjustment of registration speed" is an adjustment item for changing the speed for adjusting an image position. This is defined to belong to a display group "quality". "Smearing correction" is an adjustment item for changing a transfer speed when a sheet is transformed due to an uneven water content, causing a sheet conveying defect and resulting in an image turbulence or density nonuniformity. This is defined to belong to a display group "quality". "Fixing pressure adjustment" is an adjustment item for changing fixing pressure. This is defined to belong to a display group "quality".

"Fixing speed adjustment" is an adjustment item for changing a fixation speed. This is defined to belong to a display group "quality".

"Image position adjustment" is an adjustment item for changing a printing position on a front and back sides of a sheet. This is defined to belong to a display group "image position". "Leading/trailing edge margin adjustment" is an adjustment item for changing the lengths of margins on the leading edge side and the trailing edge side in the conveying direction for printing. This is defined to belong to a display group "image position". "Horizontal registration automatic adjustment" is an adjustment item for adjusting to prevent a target image from being displaced in a vertical (landscape) direction about the conveying direction. This is defined to belong to a display group "image position". "Sheet sorting fan airflow adjustment" is an adjustment item for changing an air flow of a fan for sorting sheets. This is defined to belong to a display group "sheet conveyance". "Pre-fixing conveying fan air flow adjustment is an adjustment item for changing an airflow of a pre-fixing convey fan. This is defined to belong to a display group "sheet conveyance".

The pull-down menu 755 is a pull-down menu by which a filter can be selected for filtering and displaying the adjustment item list 754 group by group. For example, if "quality" is selected in the pull-down menu 755, the controller 300 controls the user interface control unit 352 to display only adjustment items having a display group of "quality" in the adjustment item list 754.

Figure 13A:
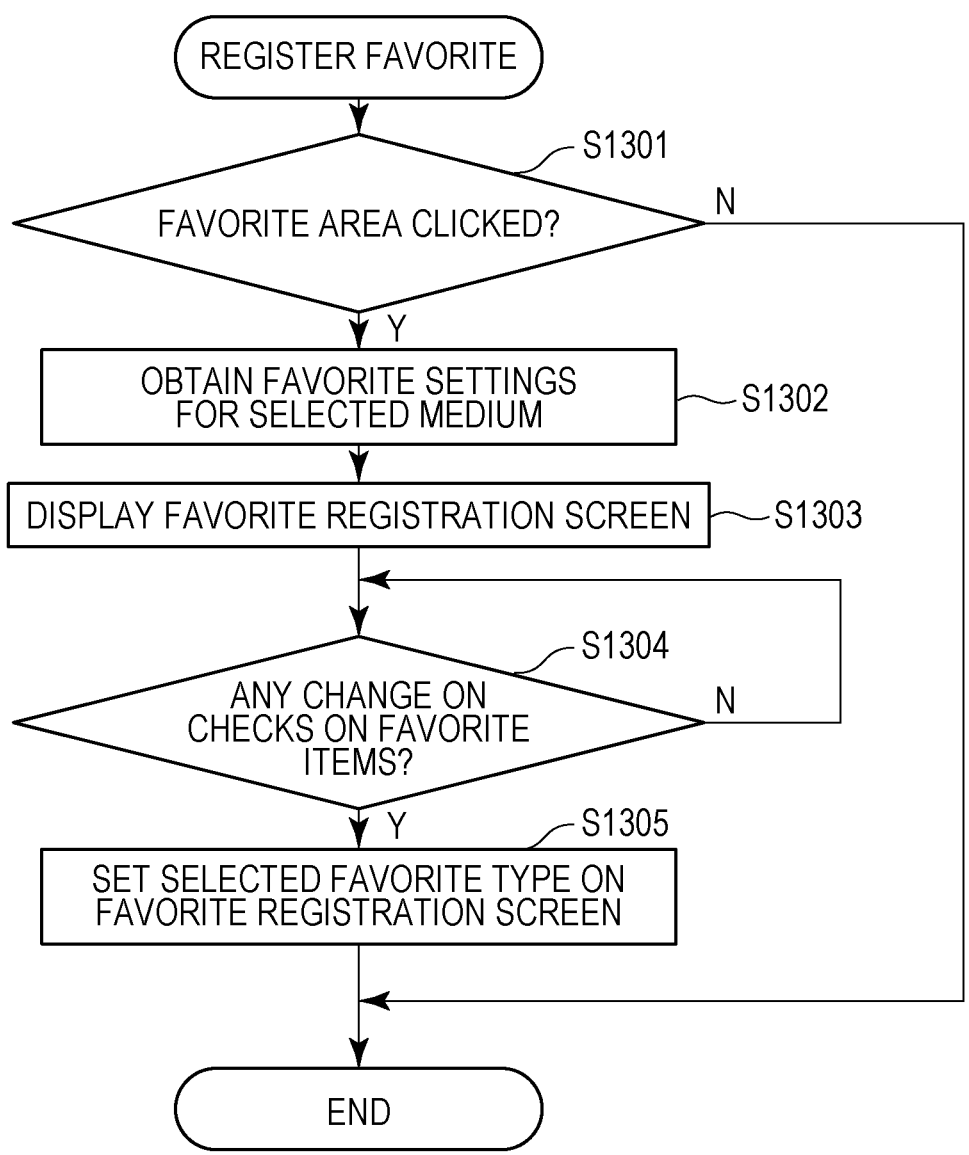
FIG. 13A illustrates a flow of a favorite registration process.

Next, a unit for setting a favorite by performing a right clock operation on the paper information list screen 730 will be described with reference to FIGS. 10A and 10B and FIG. 13A.

Figure 13B:
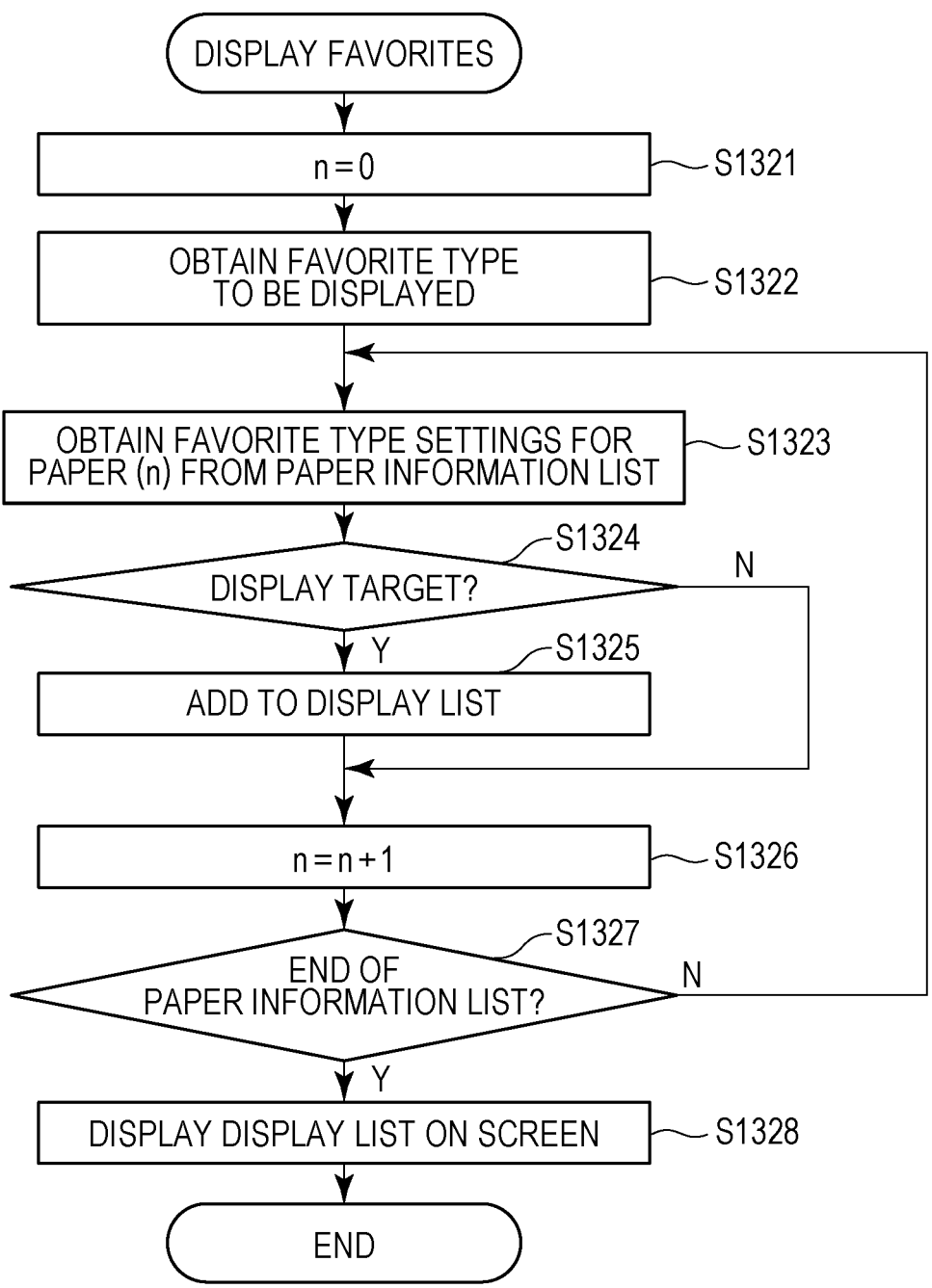
FIG. 13B illustrates a flow of a favorite display.

FIGS. 10A and 10B illustrates a screen transition for favorite registration. FIG. 13A illustrates a flow of favorite registration processing. FIG. 13B illustrates a flow for favorite display.

In step S1301, if a right-click is detected on the paper information list screen 1010, the controller 300 controls the user interface control unit 352 to determine whether a favorite icon area 1011 for a paper that is being displayed has been right-clicked. For example, in the paper information list display area 771, the first column may be a column for favorite icon display. The controller 300 controls the user interface control unit 352 to obtain the clicked row number and column number and determines whether the column number is matched with the number of the column for favorite icon display. Which paper is being selected, that is, which row in the paper information list display area 771 has been clicked is determined based on the clocked row number. The controller 300 obtains a type of click from the user interface control unit 352 and determines whether it is a right-click or not.

In step S1302, the controller 300 controls the user interface control unit 352 to obtain a favorite ID of a medium selected based on the clocked row number and column number.

In step S1303, the controller 300 controls the user interface control unit 352 to display a registered favorite menu 1021 on the paper information list screen 1020. For example, the controller 300 obtains the favorite setting table 1230 from the setting managing unit 357 and controls the registered favorite menu 1021 to embed (provide) the name of favorite and icon to be displayed. The controller 300 controls the user interface control unit 352 to check a matched favorite ID among favorites in the registered favorite menu 1021 based on the favorite settings for the paper obtained in selected step 1302. In the registered favorite menu 1021, a plurality of favorites can be checked.

In step S1304, the controller 300 controls the user interface control unit 352 to detect a change in state of the checkboxes of favorites. More specifically, whether a checkbox in the registered favorite menu 1021 is clicked is detected. For example, if Clientele Company C is clicked in the registered favorite menu 1021, the controller 300 controls the user interface control unit 352 to check the checkbox for the Clientele Company C. The processing then is controlled to move to step S1305. If Clientele Company C is not clicked, the controller 300 continues the detection processing. If an area excluding the registered favorite menu 1021 is clicked, the controller 300 controls the user interface control unit 352 to close the registered favorite menu 1021.

In step S1305, the controller 300 (paper managing unit 353) controls the areas of the paper setting management table 1210 for the currently selected paper. Thus, the favorite ID or IDs having a check in the registered favorite menu 1021 is or are overwritten. If no favorites are checked, "Not Set" is defined for the favorite ID in the paper setting management table 1210. When the writing to the paper setting management table 1210 completes, the controller 300 controls the user interface control unit 352 to close the registered favorite menu 1021. The controller 300 controls the user interface control unit 352 to update an icon for a favorite based on a favorite ID of the paper information list display area on the paper information list screen 1020 and paper settings screen 770 that are being displayed. If one favorite ID is selected, the controller 300 displays an icon corresponding to the favorite ID. If two or more favorite IDs are set, the controller 300 displays an icon indicating that a plurality of favorites are set that is different from the icon of the favorite to be registered in the registered favorite menu 1021. For example, it may be icons like objects 1022 in FIG. 10B. If no favorite ID is set, the controller 300 does not display a favorite icon.

Up to this point, the favorite setting unit has been described which is applied when the favorite icon that is being selected on the paper information list screen 1010 is right-clicked. Having described the favorite setting unit with a right-click for one selected paper for convenience of description, a plurality of paper information pieces may be selected and be right-clicked so that all of the selected paper information pieces can be registered as favorites simultaneously. For example, on the paper information list screen 1010, a plurality of paper information pieces may be selected with Ctrl+left click, and the favorite icon area 1011 may be right-clicked. The controller 300 in step S1303 controls the user interface control unit 352 to display to uncheck all of favorites in the registered favorite menu 1021. In step S1304, the controller 300 detects which favorite is checked. The processing then moves to step S1305. In step S1305, the controller 300 controls the paper managing unit 353 to perform processing for writing favorite IDs on the paper setting management table 1210 corresponding to all paper IDs that are currently being selected. A result of a logical OR of a favorite ID currently set for a paper ID to be written and the favorite ID checked in the registered favorite menu 1021 is written. For example, in a case where paper information pieces with paper ID=1, 2 are currently being selected and Clientele Company B is checked in the registered favorite menu 1021, the favorite ID of the paper ID=1 is written with 1, 2. The favorite ID of the paper ID=2 is also written with 1, 2.

Having described that, according to this embodiment, the registered favorite menu 1021 is presented in response to a right-click as an example, embodiments of the present disclosure are not limited to the right-click. For example, the registered favorite menu 1021 may be displayed in response to a press of a shortcut key or a specific key on the keyboard. Alternatively, a press of a combination of specific keys may enable registration of a favorite corresponding to the keys without presenting the registered favorite menu 1021.

Favorite Display Unit

Next, the aforementioned information on favorites will be used to describe a flow for printing a house leaflet by an operator with reference to FIG. 6B.

In step S601, an operator may press the paper information list button 711 on the top screen 710 in the paper management system.

In step S602, the controller 300 in the print control apparatus 102 controls the user interface control unit 352 to obtain the paper setting management table 1210 from the paper managing unit 353. The controller 300 controls the user interface control unit 352 to create a paper information list screen 910 based on the obtained paper information list.

Next, details of the paper information list screen will be described with reference to the paper information list screen 730 in FIG. 7A. In response to an instruction from the CPU 301, the paper information list screen 730 renders data in its video memory, and image data rendered in the video memory are output as a video signal to the display device 111 for display. The screen 730 displays the paper information list display area 731, a pull-down menu 732 for selecting a paper information list display method, a paper search input area 733, and buttons (paper add buttons) for adding a paper to a paper information list. The paper add button to be displayed may include a new registration button 734 for registering a new paper to the paper information list, a copy button 735 for copying an existing paper to the paper information list, and a registration button 736 for generating a paper from a paper information database.

Figure 9A:
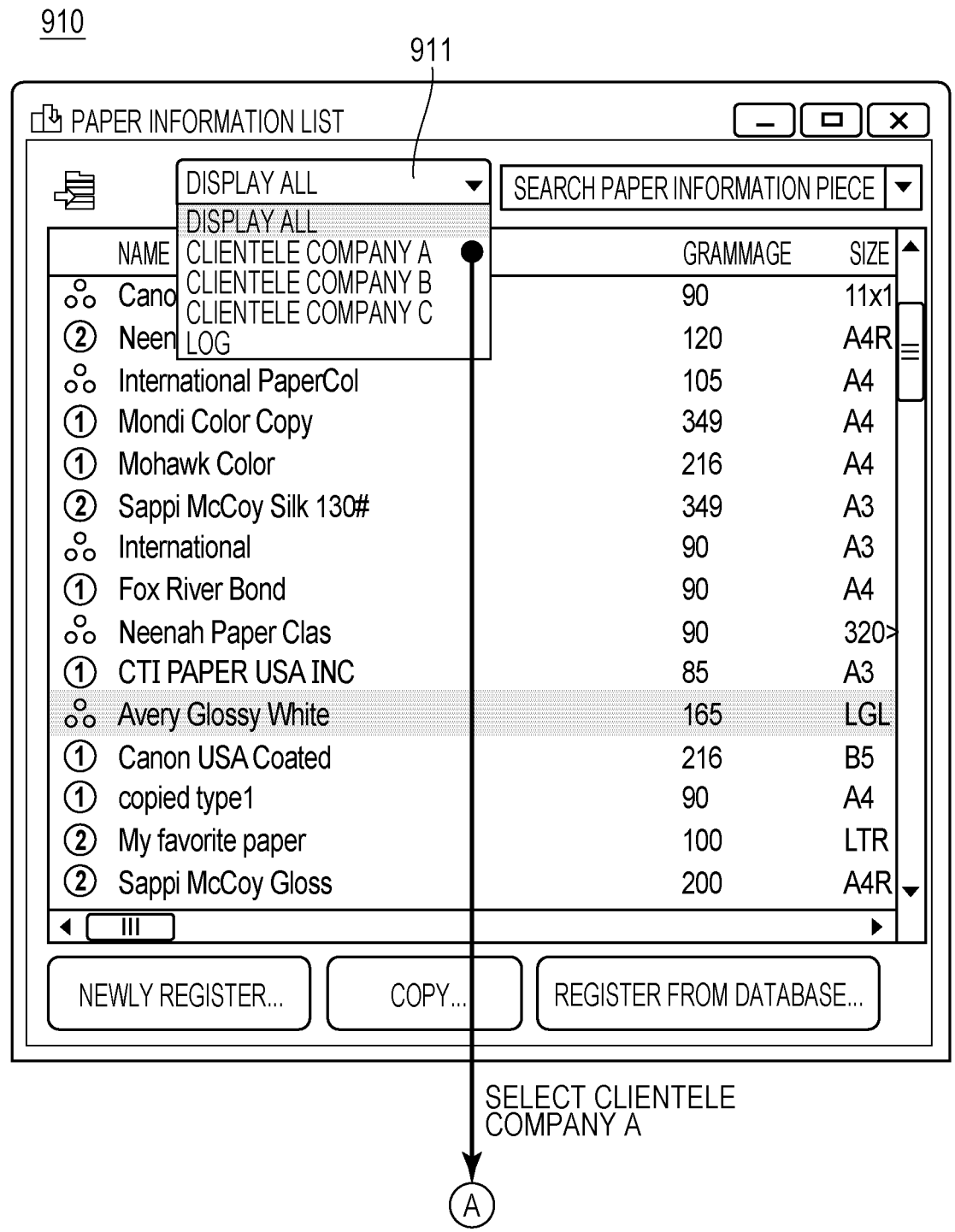
Figure 9B:
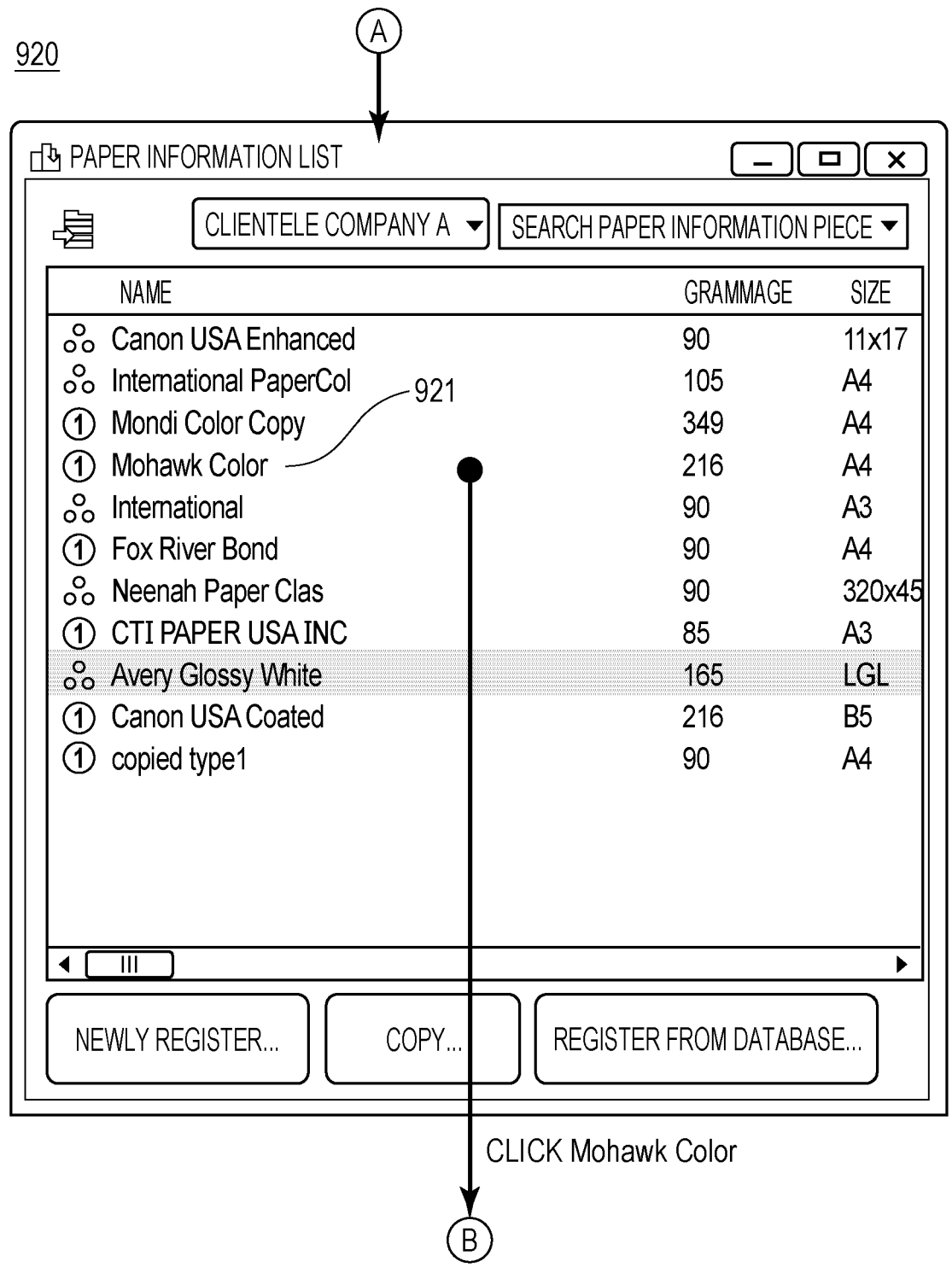

FIGS. 9A to 9C illustrate screen transitions for registering a paper information piece with a paper-feed stage. The paper information list display area of an object 731 in FIG. 7A will be described. The object 731 is a table displaying a paper information list. The table has a column indicating paper information and a row indicating set paper information pieces. In order to display information other than attribute information of the displayed paper information pieces, a slider bar of an object 737 can be operated to display the information. In order to display a paper other than displayed paper information pieces, a slider bar of an object 738 may be operated to display the paper. A paper that is being selected is highlighted so that it can clearly inform that the paper information piece is being selected. If one of paper information pieces that are not being selected from the table displaying the paper information list of the object 731, information regarding the paper information piece that is currently being selected is displayed in a paper information list area 731. According to this embodiment, if a column 739 displaying "favorite" icons is right-clicked, a registered favorite menu 1021 in FIG. 10B is displayed. If another column 740 is right-clicked, a paper-type registered context menu 932 in FIG. 9C is displayed. Having described that the column 739 and the column 740 undergo different processes from each other, when either one of the columns is left-clicked, the left-clicked paper is commonly selected. In a case where a plurality of paper information pieces are being selected and when the column 740 is right-clicked, the controller 300 may control the user interface control unit 352 not to display the paper-type registered context menu 932, for example. This is because a plurality of paper information pieces is not set for one paper-feed stage. Alternatively, a plurality of selections may be canceled, and the column or icon corresponding to a certain paper that is clicked finally may be selected. Then, the paper-type registered context menu 932 may be controlled to display for the paper that is being selected (finally clicked paper information column or icon).

A pull-down menu for selecting a method for displaying the paper information list 732 will be described. The pull-down menu 732 displays how the paper information list display area of the object 731 is to be displayed. According to this embodiment, one of "Display All", "Clientele Company A", "Clientele Company B", "Clientele Company C", "Log" may be selected for display. Assume that "Display All" is selected for display here.

The terms "Clientele Company A", "Clientele Company B", and "Clientele Company C" are selection options for filtering display contents for the paper information list display area of the object 731 for each favorite ID of a paper information piece.

In step S603, the controller 300 controls the user interface control unit 352 to display the paper information list screen 910 on the display device 111.

In step S604, an operator may select "Clientele Company A" in the pull-down menu 732.

In step S605, the controller 300 (by controlling the user interface control unit 352) detects a change in the pull-down menu 911. The controller 300 generates a paper information list based on the selection in the pull-down menu 911 according to the paper information in the paper setting management table 1210. For example, if "Clientele Company A" is selected in the pull-down menu 911 as illustrated in FIG. 10, the controller 300 refers to favorite IDs of paper information pieces in the paper setting management table 1210 to determine whether "Clientele Company A" (favorite ID=1) is included therein or not. The controller 300 controls the user interface control unit 352 to add a matched paper to the paper information list display area 731. With reference to the flowchart in FIG. 13B, a flow of processing will be described.

In step S1321, the controller 300 controls the user interface control unit 352 to set 0 for the initial value of a row number n in a paper information piece displayed in the paper information list display area 731.

In step S1322, the controller 300 controls the user interface control unit 352 to refer to a selected item in the pull-down menu 911 to obtain a favorite to be displayed. Here, as a favorite, Clientele Company A (favorite ID=1) can be obtained.

In step S1323, the controller 300 controls the paper managing unit 353 to obtain a paper information piece at an (n+1) the row (first row) in the paper setting management table 1210 and refer to the favorite ID of the obtained paper information piece. Assume here that favorite ID=1 for a paper of (Mohawk Color) is obtained.

In step S1324, the controller 300 controls the user interface control unit 352 to determine whether the favorite ID obtained in step S1323 is matched with the favorite ID obtained in step S1322. Here, whether it is matched with favorite ID=1 is determined. If matched, the controller 300 advances the processing to step S1325. If not, the controller 300 advances the processing to step S1326. Because the favorite ID of the paper (Mohawk Color) is matched with the favorite ID=1, the processing moves to step S1325.

In step S1325, the controller 300 controls the user interface control unit 352 to add the paper information piece at the (n+1) the row to the paper information list display area

731. The controller 300 here adds the sheet (Mohawk Color) to the paper information list display area 731.

In step S1326, the controller 300 controls the user interface control unit 352 to increment by 1 (one) the row number n in the paper information piece to be displayed in the paper information list display area 731.

In step S1327, the controller 300 controls the paper managing unit 353 to determine whether the processing reaches the end of the paper setting management table 1210 or not. If the processing reaches the end, the controller 300 advances the processing to step S1328. If not, the controller 300 advances processing to the step S1323 whether the processing in step S1323 to step S1326 is performed on paper information pieces in the rest of the paper setting management table 1210. Here, because more paper information pieces remain in the paper setting management table 1210, the controller 300 advances the processing to step S1323. The controller 300 controls the paper managing unit 353 to obtain a paper information piece of the (n+1) the row (or second row) of the paper setting management table 1210 and performs the processing in step S1323 to step S1326.

In step S1328, because only paper information pieces matched with the selected item in the pull-down menu 911 are ready for display in the paper information list display area 731, the controller 300 controls the user interface control unit 352 to display a paper information list screen 920. In a case where there is a paper having a plurality of favorite IDs (such as paper information pieces in the table 1210 in FIG. 12A (paper ID=2)), either Clientele Company A or Clientele Company B may be selected in the pull-down menu 911 to display the paper information list display area 731.

Referring back to FIGS. 6A and 6B, in step S606, the controller 300 controls the user interface control unit 352 to display the paper information list screen 920 including the paper information list display area 731 having undergone filtering with "Clientele Company A" in step S605. In other words, the paper information list screen 920 can display a list of paper information pieces associated with Clientele Company A.

If the column 739 is clicked independently from the selected item in the pull-down menu 911, the menu 1021 displays all favorites. For example, even when Clientele Company A is selected in the pull-down menu 911, it is determined that the object 1021 displays "Clientele Company A", "Clientele Company B", and "Clientele Company C".

In step S607, an operator may select the paper information piece (Mohawk Color) 921 by left-clicking for use in printing in association with Clientele Company A. The controller 300 controls the user interface control unit 352 to cause the paper information 921 selected by left-clicking to have a selected state, like the paper information 931. The operator may right-click a name area for allocation of the paper to a paper-feed stage.

In step S608, if the controller 300 detects a right-click at a column other than a favorite icon as described with reference to the column 740 in FIG. 7A, the controller 300 controls the user interface control unit to generate a paper-type registered context menu 932. The controller 300 controls to obtain a settable paper-feed stage ID in the paper setting management table 1210 corresponding to the paper 931 from the paper managing unit 353 and obtain the corresponding paper-feed stage name from the paper-feed stage management table 1220. For example, in the examples in FIGS. 9A to 9C, the controller 300 obtains settable paper-feed stage IDs={1, 2, 3, 4, 5} for the paper 931 (paper ID=1) and obtains a paper-feed stage name of each of the paper-feed stage IDs from the paper-feed stage management table 1220. In this example, IDs corresponding to a paper cassette 1, a paper cassette 2, a paper cassette 3, a paper cassette 4, and a manual feed tray are obtained, and the controller 300 controls the user interface control unit 352 to generate a paper-type registered context menu 932.

In step S609, the controller 300 controls the user interface control unit 352 to display the paper-type registered context menu 932.

In step S610, an operator may select a paper-feed stage (paper cassette 1) with which the paper is to be registered from the paper-type registered context menu 932.

In step S611, the controller 300 controls the paper managing unit 353 to generate a paper setting instruction for registering information in the paper setting management table 1210 corresponding to the selected paper 931 with the paper cassette 1 (paper-feed stage ID=5). The controller 300 controls the network control unit 355 to transmit the paper setting instruct to the image forming apparatus 103 via a control cable 108 under control of the LAN controller 306.

In step S612, the controller 200 in the image forming apparatus 103 in response to the paper setting instruction received under the LAN controller 206 sets the received paper information piece for the paper 931 for the designated paper-feed stage (paper cassette 1 here). Having described how a paper information piece is to be set by right-clicking with reference to FIGS. 6A and 6B, the paper 931 can be dragged as illustrated in FIGS. 9A to 9C and be dropped to the paper-feed stage button 941 for the paper cassette 1 on the top screen 940 to set the paper, according to this embodiment. The controller 300 counts up the usage log of the paper having been set and controls the paper managing unit 353 to write the count to the usage log in the paper setting management table 1210 for the target paper ID.

In step S613, the operator may open the paper cassette 1 in the image forming apparatus 103 and set a paper bundle of the paper 931. The operator may then close the paper cassette 1.

Up to this point, the procedure for defining a paper to be used for printing has been described. Next, a flow for printing a job 1 of Company A by using the paper 931 will be described.

In step S614, the operator may generate a Company A job 1 by using the client computer 101, changes settings to use the paper 931, and transmits a print instruction to the print control apparatus 102 by using a print application or a printer driver. The print instruction includes designations of a paper and a paper-feed stage to be used for printing and is designated through a user interface of the print application or the printer driver when instructing to print. The client computer 101 transmits Page Description Language (PDL) data as an execution instruction for the print processing to the print control apparatus 102. According to this embodiment, the PDL data designates a paper or a paper-feed stage to be used for the printing. Assume here that the paper cassette 1 is designated as a paper-feed stage by using the user interface of the printer driver.

In step S615, the controller 300 in the print control apparatus 102 performs RIP (Raster Image Processor) processing based on the received PDL data and generates raster image data which can be readable by the image forming apparatus 103. The controller 300 analyzes the print instruction included in the PDL data and generates print setting information used for the print processing.

In step S616, the controller 300 transmits the image data and print setting information used for the print processing as print data to the image forming apparatus 103. Here, assume that the paper cassette 1 is designated as the paper-feed stage in the print data. According to this embodiment, the controller 300 controls the network control unit 355 to transmit the print setting information to the image forming apparatus 103 via the control cable 108 under control of the LAN controller 306. The controller 300 controls the job managing unit 356 to transmit the image data to the image forming apparatus 103 via the image video cable 107 through the video interface 310.

In step S617, the controller 200 in the image forming apparatus 103 controls to feed paper from the designated paper-feed stage or the paper-feed stage, with which the paper is registered based on the received print data. Because the paper cassette 1 is designated as the paper-feed stage in the print data, the paper cassette 1 is to be used.

In step S618, the controller 200 controls the printing unit (printer engine) 213 connected thereto to output and print image signal that is output information through the print interface 207.

The flow of the processing for finding a desired paper and performing printing with it by using the favorite display has been described up to this point. Thus, an operator can easily find a paper (Mohawk Color for Clientele Company A) desired by the operator even in a case where a desired paper is settled for each of a plurality of clienteles (customers). This can improve convenience of the operator who perform the paper setting operation relating to paper for a digital multi function peripheral.

Embodiment 2

In a case where many favorite paper information pieces are set by the favorite setting unit according to Embodiment 1, it may be difficult to quickly find a paper information piece even on a displayed list of favorites. For example, assume a case where "Clientele Company A", "Clientele Company B", and "Clientele Company C" are prepared as favorites and where paper information pieces to be used for each of the favorites are preset. However, the types of printed products ordered by Clientele Company A may increase, requiring scrolling through paper information pieces belonging to Clientele Company A. It may be difficult for an operator to find a desired paper information piece even by performing filtering with "Clientele Company A" in the pull-down menu 732 on the paper information list screen 730 for printing for Clientele Company A.

Accordingly, in a second embodiment, when such a circumstance occurs, an unnecessary favorite paper information piece can be deleted to maintain a state in which a desired favorite paper information piece can easily be found. More specifically, if, after implementing the favorite setting, the total number of paper information pieces having set as favorites reaches a predetermined threshold value, a screen for cancelling the favorite setting is to be displayed.

Figure 14A:
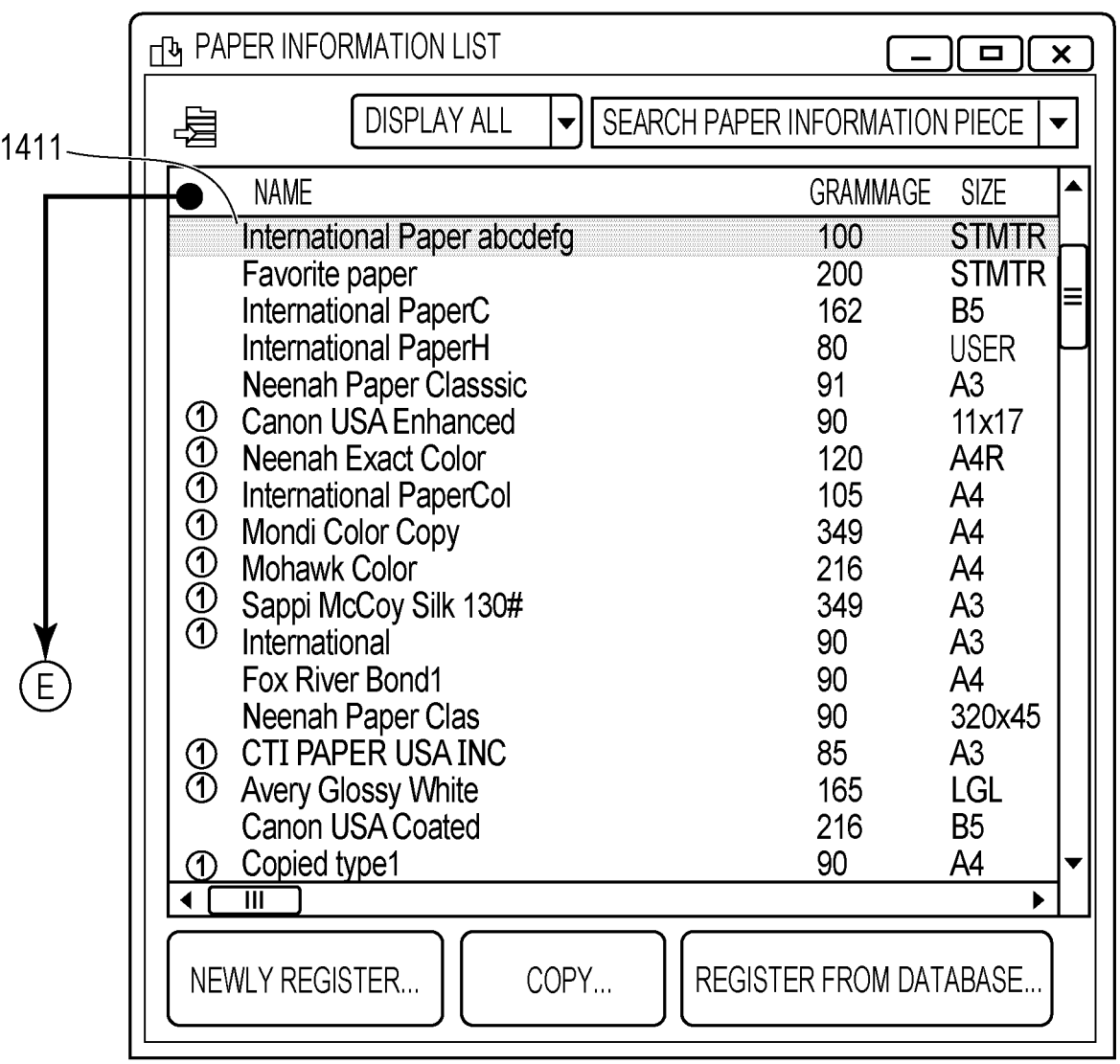
FIGS. 14A to 14C illustrate screen transitions for a favorite registration.
Figure 14B:
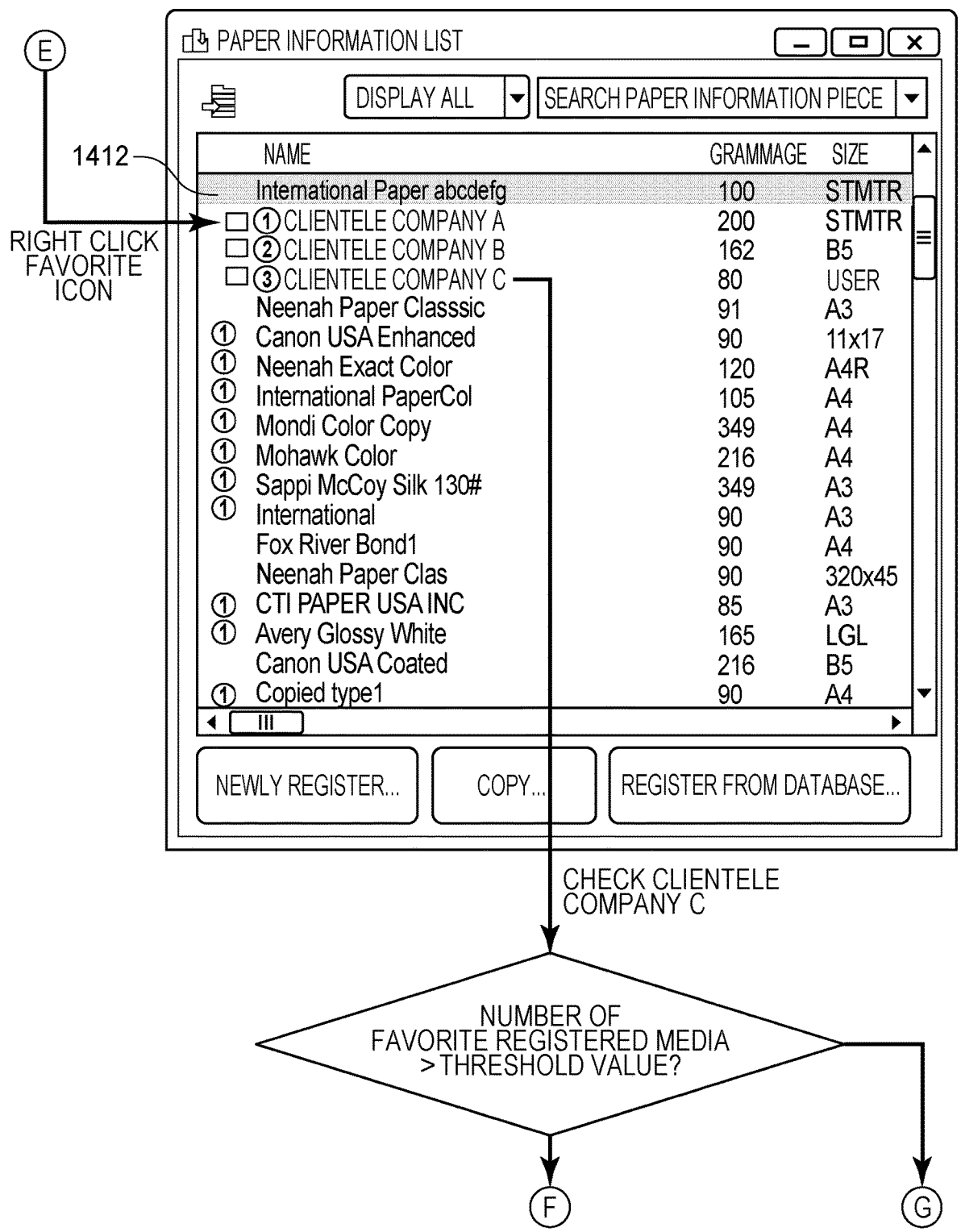
Figure 14C:
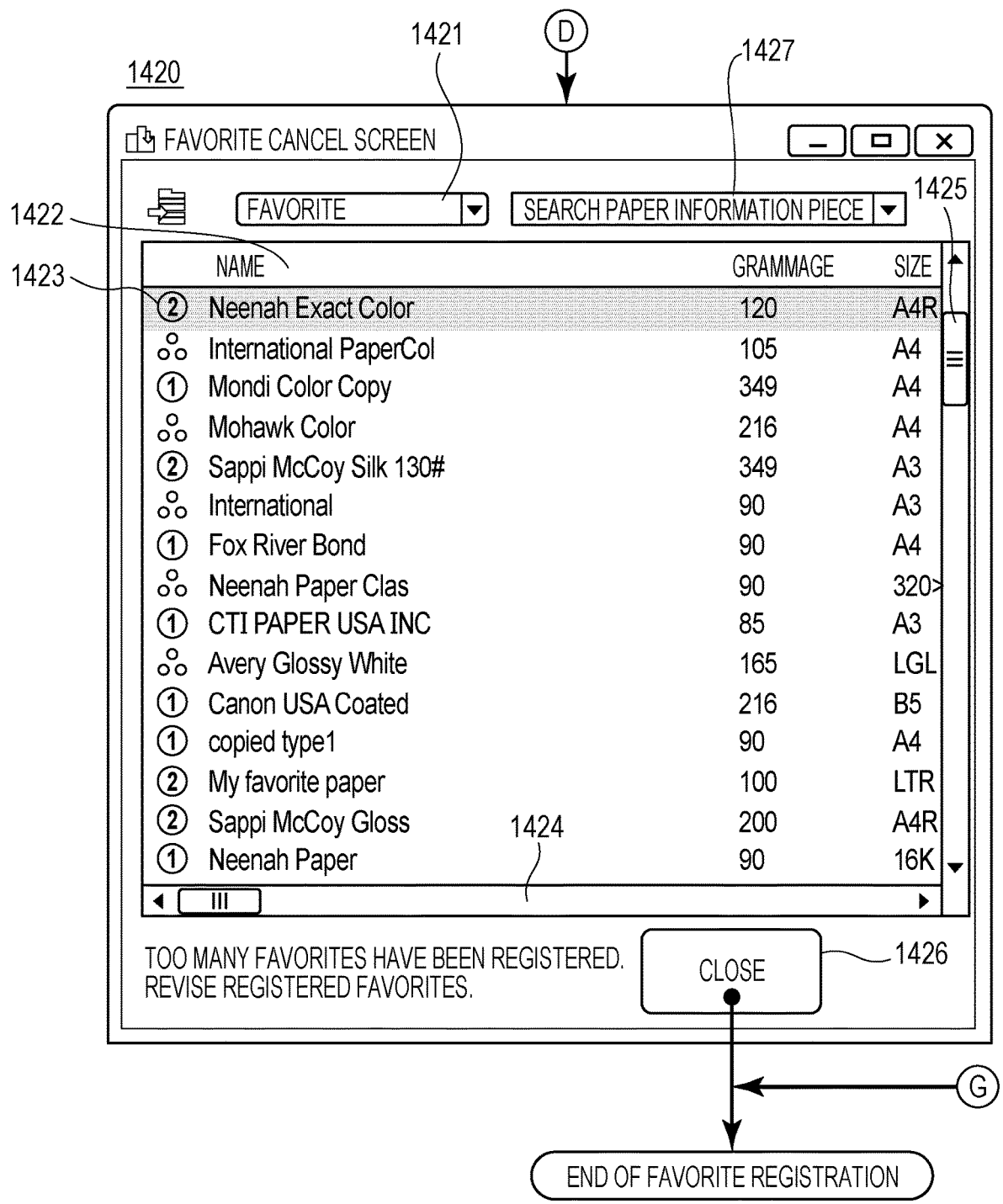

Processing according to this embodiment will be described with reference to FIGS. 14A to 14C and FIG. 15. FIGS. 14A to 14C illustrate screen transitions for a favorite registration. FIG. 15 illustrates a flow of a favorite registration process. Because the favorite registration process has described according to Embodiment 1, any repetitive descriptions will be omitted. On a paper information list screen 1410 in FIG. 14A, when a paper information piece 1411 is being selected, an operator may right-click a favorite icon area 1412. The operator may check "Clientele Company C" in a registered favorite menu 1413.

With reference to the flowchart in FIG. 15, the process will be described below.

In step S1501, the controller 300 controls the paper managing unit 353 to calculate a total number of paper information pieces set for a favorite and determines whether it is higher than a predetermined threshold value. For example, a total number of paper information pieces set for a favorite can be calculated with reference to paper information in the paper setting management table 1210 and counts the number of paper information pieces for which favorite IDs are set. If the total number of paper information pieces set for a favorite is higher than the threshold value, the controller 300 advances the processing to step S1502. If the total number of paper information pieces set for a favorite does not exceed the threshold value, the favorite configuration processing ends without performing anything.

In step S1502, in order to display a favorite cancel screen 1420, the controller 300 controls the paper managing unit 353 to generate a paper information list display area 1422 to which paper information pieces belonging to a certain favorite are only added. The favorite cancel screen 1420 is a screen on which a favorite registration set to paper information can be cancelled. The favorite cancel screen 1420 displays a message prompting to cancel the registration. Because the basic processing flow is the same as the processing flow in step S1321 to S1327 in FIG. 13B, differences therebetween will only be described below.

Because the processing in step S1321 is performed in the same manner as described above, it will not be described repetitively here.

In step S1322, the controller 300 handles all of favorite IDs in the favorite setting table 1230 to be displayed as favorites. Assume that favorite IDs=1, 2, 3 are to be displayed.

Because the processing in step S1323 is performed in the same manner as described above, it will not be described repetitively here.

In step S1324, the controller 300 determines whether the favorite ID of the paper information of the (n+1) the row in the paper setting management table 1210 is matched with one of the favorite IDs=1, 2, 3. If it is matched with one of the favorite IDs, the processing moves to step S1325. If not, the processing moves to step S1326.

Because the processing in step S1326 is performed in the same manner as described above, it will not be described repetitively here.

Because the processing in step S1327 is performed in the same manner as described above, it will not be described repetitively here. Through the processing up to this point performed on all of the paper information in the paper setting management table 1210, the processing in step S1502 completes.

In step S1503, the controller 300 controls the user interface control unit 352 to sort paper information pieces in the paper information list display area 1422 generated in step S1502 in increasing order (ascending order) of the number of usage logs of the display areas.

In step S1504, the controller 300 controls the user interface control unit 352 to display the favorite cancel screen 1420.

The favorite cancel screen 1420 includes a pull-down menu 1421 for selecting a method for displaying a paper information list, a paper information list display area 1422, paper information search input area 1427, and a button 1426 for closing the favorite cancel screen 1420. The paper information list display area 1422 has slider bars 1424, 1425 similar to the slider bars 737, 738. Because these components are the same as those of the paper information list screen 730 except for the pull-down menu 1421, any repetitive descriptions will be described. They are different in that a selection option "favorite" is displayed which means one of favorites in the pull-down menu 1421 is applicable. Here, "favorite" means that one of the favorite IDs=1, 2, 3 is applicable. According to this embodiment, the favorite cancel screen 1420 may display a checkbox for selecting whether the favorite cancel screen 1420 is to be displayed from the current point.

Up to this point, deletion of an unnecessary paper information piece has been described in a case where the number of favorite paper information pieces is equal to or higher than a predetermined number. Thus, when the number of registered favorites increases, a guidance may be given to a screen prompting to delete an unnecessary favorite paper information piece for easily finding a desired paper information piece. Because of deletion of an unnecessary favorite paper information piece, an operator can keep easiness of finding of a desired paper information piece easily. Therefore, the operator can easily find a desired paper information piece.

Embodiment 3

According to Embodiment 2, an unnecessary paper information piece is deleted in a case where the number of favorite paper information pieces increases. However, selecting and cancelling paper information pieces one by one through the favorite cancel screen requires time and labor. Particularly in a case where there is an unnecessary favorite group of paper information pieces, the group itself can be deleted for easy cancellation of favorite paper information pieces by an operator.

According to this embodiment, when the circumstance (specific condition) occurs, a favorite group of paper information pieces can be deleted for keeping easiness of finding of a desired paper information piece, unlike Embodiment 2. More specifically, if, after implementing the favorite setting, the total number of paper information pieces having set as favorites reaches a predetermined threshold value, a favorite cancel screen 1620 is displayed.

Figure 16B:
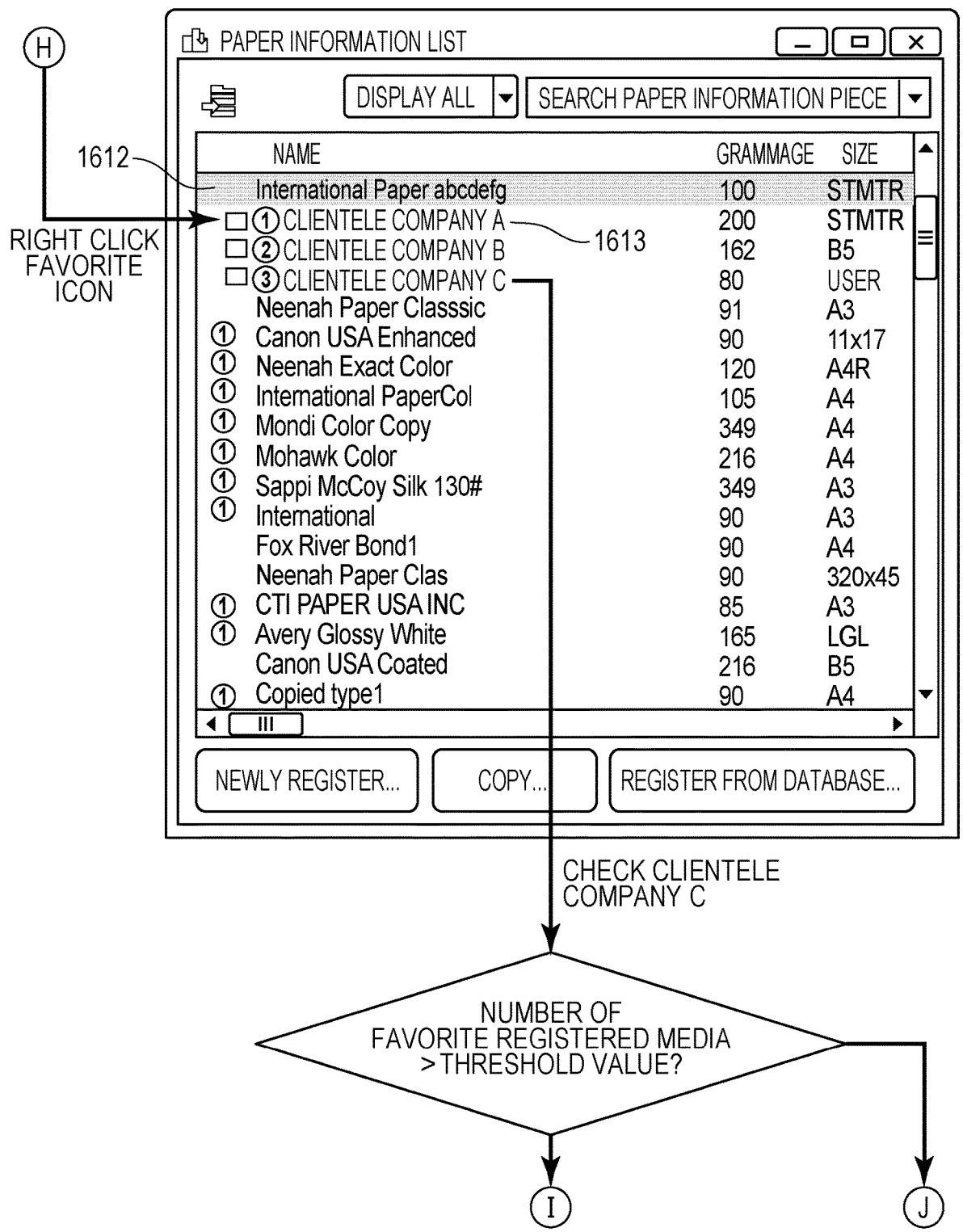
Figure 16C:
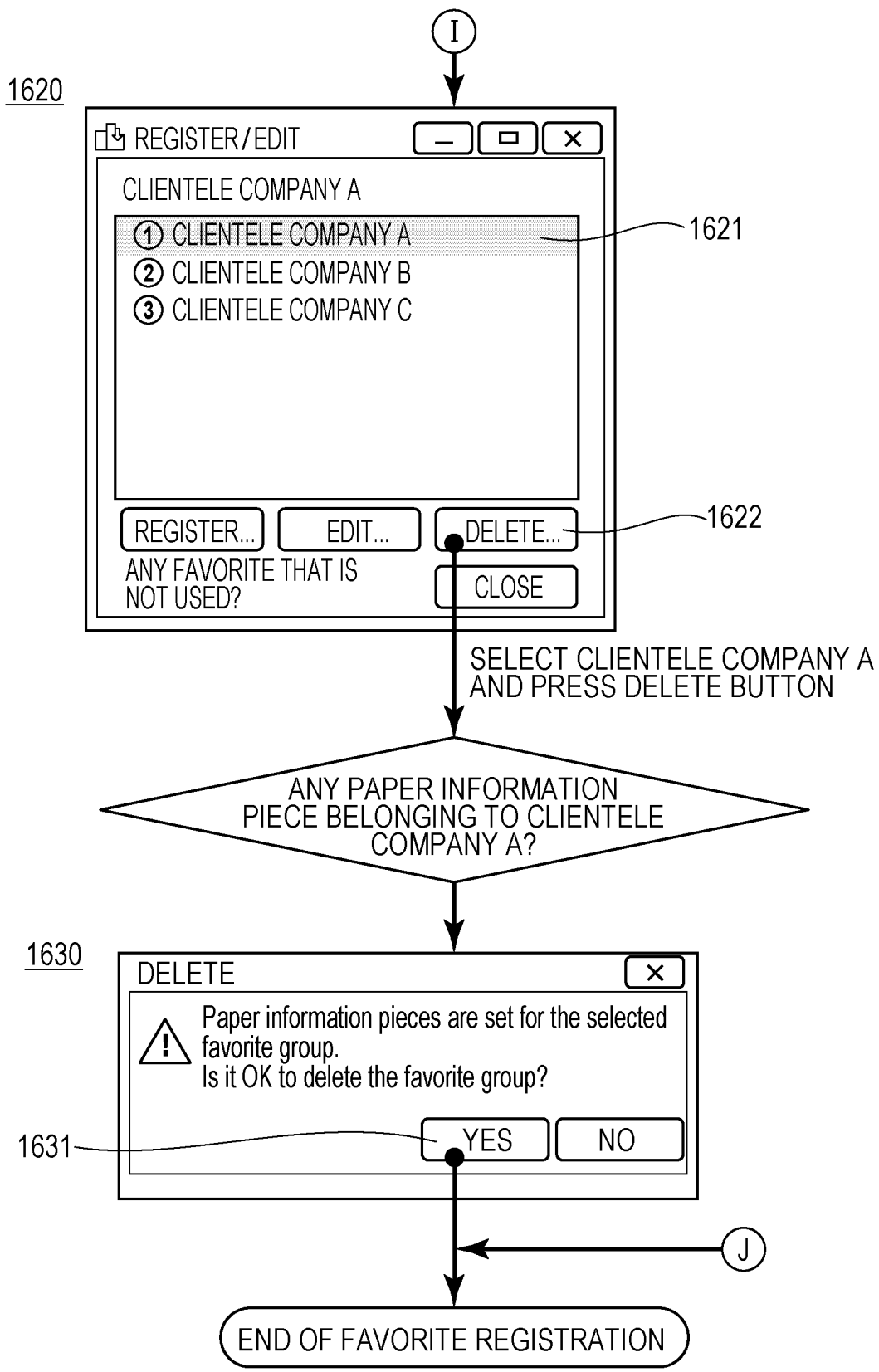
Figure 17:
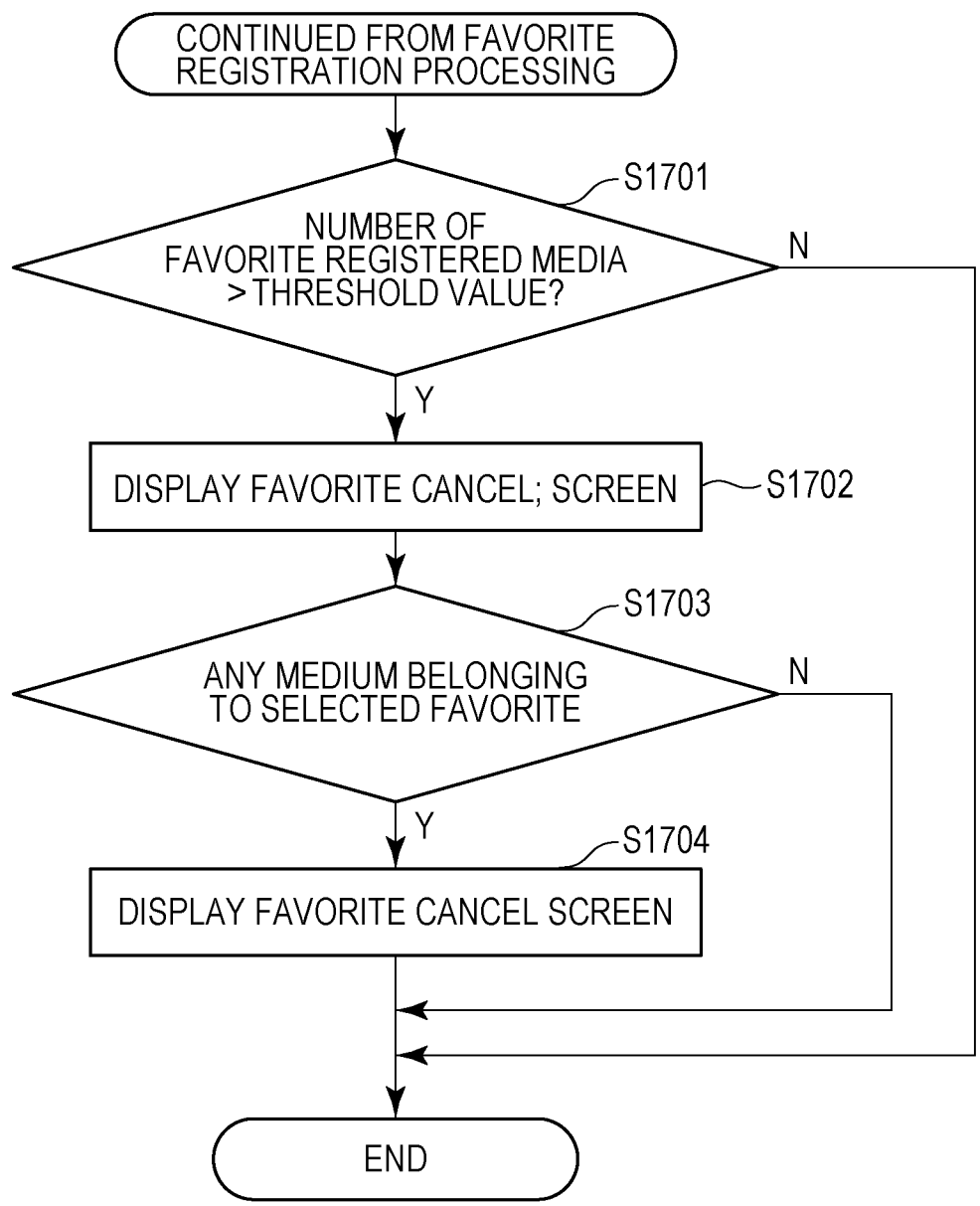
FIG. 17 illustrates a flow of a favorite registration process.

Processing according to this embodiment will be described with reference to FIGS. 16A to 16C and FIG. 17. FIGS. 16A to 16C illustrate screen transitions for a favorite registration. FIG. 17 illustrates a flow of a favorite registration process.

Because the favorite registration process has been described according to Embodiment 1, any repetitive descriptions will be omitted. On a paper information list screen 1610 in FIG. 16A, when a paper information piece 1611 is being selected, an operator may right-click a favorite icon area 1612. The operator may check "Clientele Company C" in a registered favorite menu 1613.

With reference to the flowchart in FIG. 17, the process will be described below. In step S1701, the controller 300 controls the paper managing unit 353 to calculate a total number of paper information pieces set for a favorite and determines whether it is higher than a predetermined threshold value. Because the processing is performed in the same manner as in S1501, it will not be described repetitively here. If a total number of paper information pieces set for a favorite exceeds the threshold value, the controller 300 advances the processing to step S1702. If the total number of paper information pieces set for a favorite does not exceed the threshold value, the favorite configuration processing ends without performing anything. In other words, a predetermined number of paper information pieces at a maximum can be registered normally.

In step S1702, the controller 300 displays the favorite cancel screen 1620. The favorite cancel screen 1620 has the same screen configuration as that of the favorite management screen. They are different in that a message "any favorite that is not used?" is displayed within the screen to an operator.

Because the processing in steps S1703 and S1704 is performed in the same manner as described with reference to the warning screen 1150 in the description regarding "screen transitions for deleting a registered favorite" according to Embodiment 1 with reference to FIGS. 11A and 11B, any repetitive descriptions will be omitted.

Up to this point, deletion of an unnecessary favorite group of paper information pieces has been described in a case where the number of registered favorite paper information pieces is increased. Thus, when the number of registered favorites increases, a guidance may be given to a screen prompting to delete an unnecessary favorite group of paper information pieces for easily finding a desired paper information piece. Because of deletion of an unnecessary favorite group of paper information pieces, an operator can delete unnecessary favorite paper information pieces by one operation and can keep easiness of finding of a desired paper information piece easily. Therefore, the operator can easily find a desired paper information piece.

Embodiment 4

According to Embodiments 2 and 3, when the number of favorite paper information pieces increases, an unnecessary favorite paper information piece or an unnecessary favorite group of paper information pieces is deleted. However, when the number of clienteles increases but clienteles from the past are still kept as clienteles, the current paper information pieces may necessarily be kept even though the number of paper information pieces increases.

Accordingly, in Embodiment 4, when such a circumstance occurs, an unnecessary favorite paper information piece is not deleted to maintain a state in which a desired favorite paper information piece can easily be found, unlike Embodiments 2 and 3. More specifically, if the total number of paper information pieces having set as favorites reaches a predetermined threshold value and when a paper information list screen 1810 is to be displayed, the paper information list screen 1810 is prepared for enabling a quick paper information search.

Figure 18:
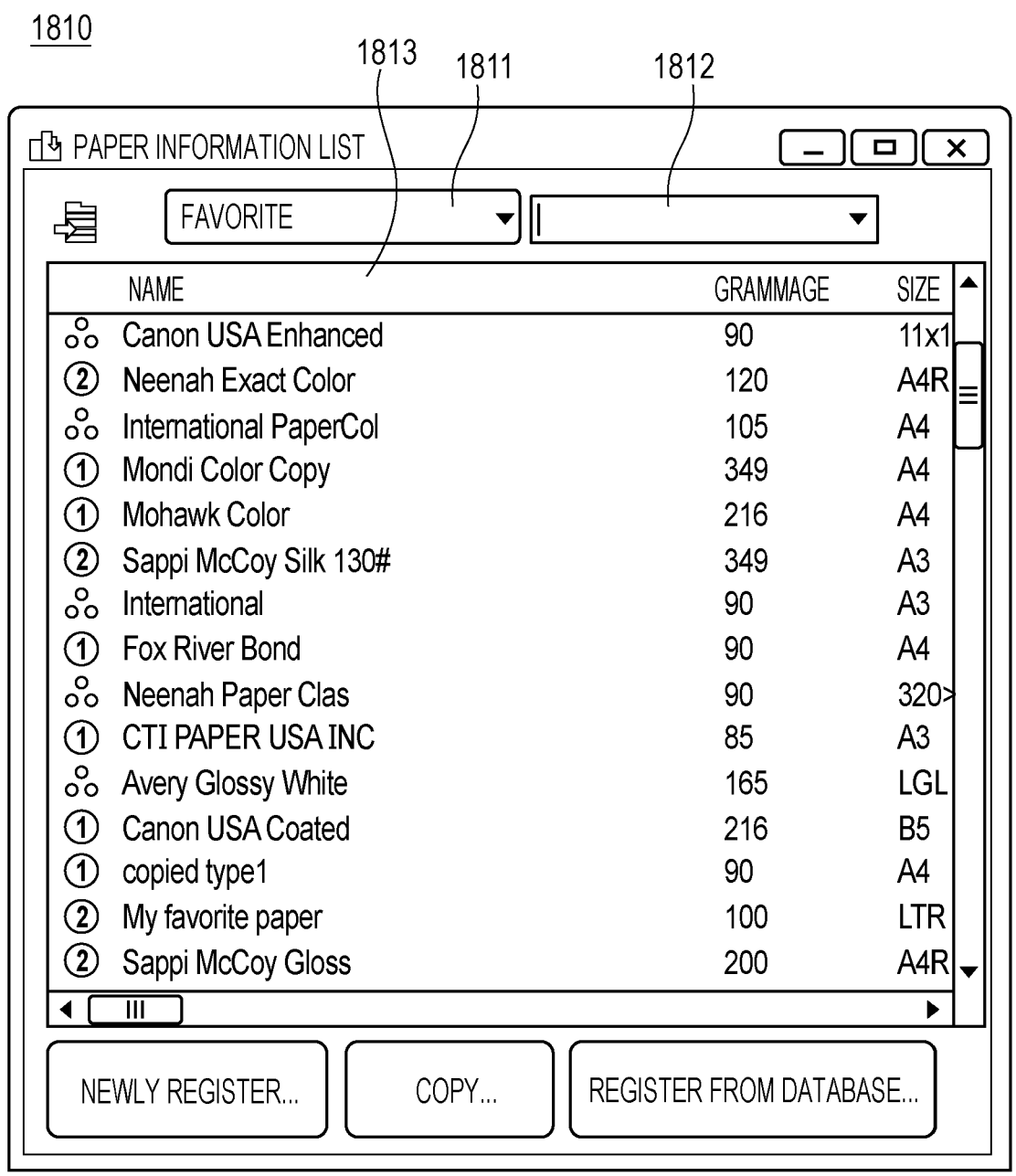
FIG. 18 illustrates a paper information list screen.
Figure 19:
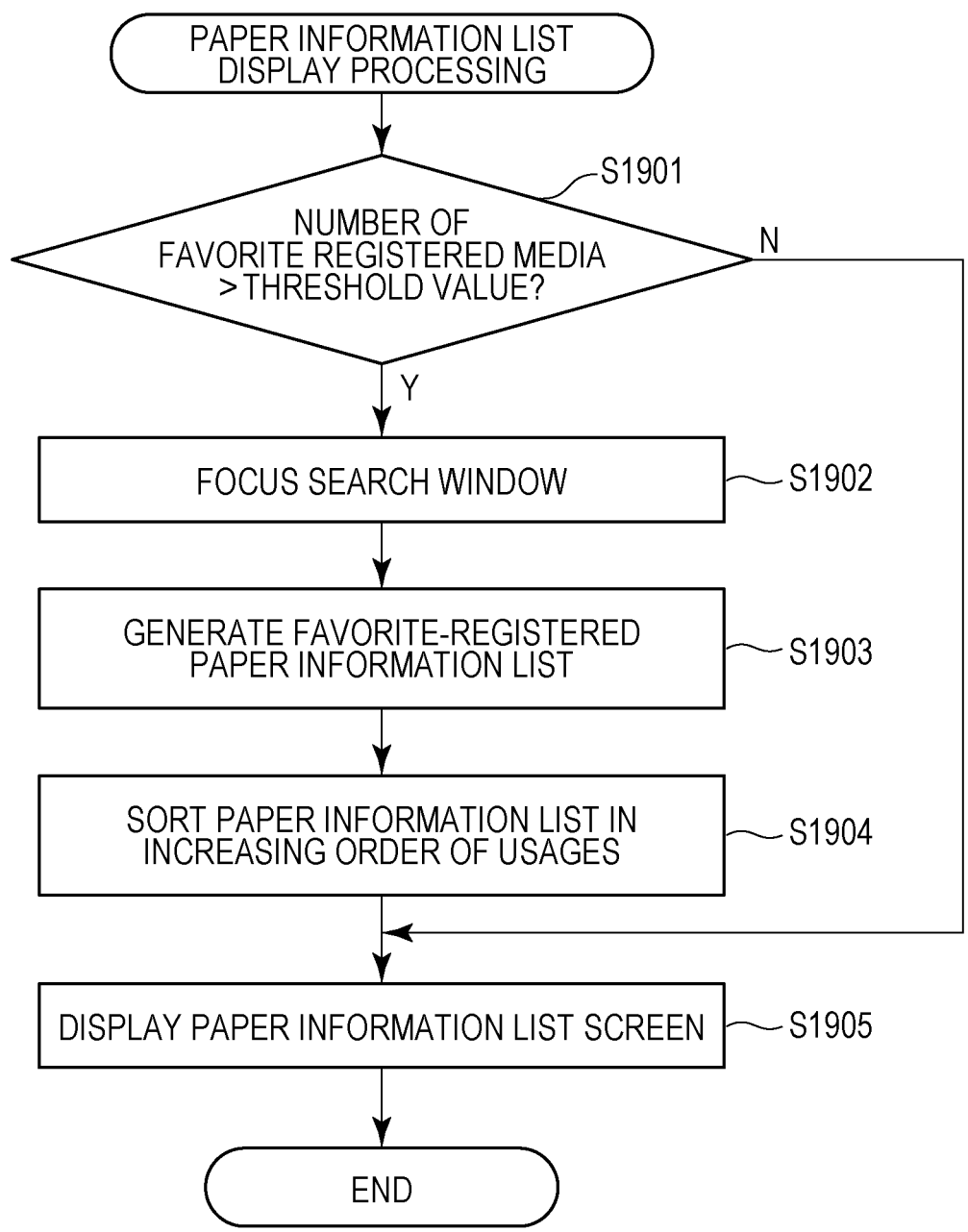
FIG. 19 illustrates a flow of processing for displaying a paper information list.

Processing according to this embodiment will be described with reference to FIG. 18 and FIG. 19. FIG. 18 illustrates a paper information list screen. FIG. 19 illustrates a flow of processing for displaying the paper information list.

With reference to the flowchart in FIG. 19, the processing will be described below. The flowchart illustrates processing to be performed in response to a press of the button 711 on the top screen or when the paper information list screen 1810 that is being displayed is rendered in the foreground.

In step S1901, the controller 300 controls the paper managing unit 353 to calculate a total number of paper information pieces set for a favorite and determines whether it is higher than a predetermined threshold value. Because the processing is performed in the same manner as in S1501, it will not be described repetitively here. If a total number of paper information pieces set as favorites exceeds the threshold value, the controller 300 advances the processing to step S1902. If the total number of paper information pieces set as favorites does not exceed the threshold value, the favorite configuration processing ends without performing anything.

In step S1902, the controller 300 controls the user interface control unit 352 to set a screen input focus in a search input area 1812.

In step S1903, the controller 300 generates the paper information list 1813 of all paper information pieces registered with favorites. Because the processing is performed in the same manner as in S1502 in FIG. 15, it will not be described repetitively here.

In step S1904, the controller 300 sorts the paper information list 1813 generated in step S1902 in order of usage logs. Because the processing is performed in the same manner as in S1503 in FIG. 15, it will not be described repetitively here.

In step S1905, the controller 300 controls the user interface control unit 352 to display the paper information list screen 1810. A selection option "favorite" is displayed which means one of favorites in the pull-down menu 1811 is applicable. Here, "favorite" means that one of the favorite IDs=1, 2, 3 is applicable.

Up to this point, it has been described that, if the number of paper information pieces registered as favorites increases, a state can be obtained in which a key word can be input quickly in the paper information search input area when the paper information list screen is displayed. Therefore, when the number of registered favorites increases, a guidance may be given to a search unit for easier finding of a desired paper information piece than cases based on favorites. As a result, an operator can easily find a desired paper information piece even in a case where a significantly large number of favorites are registered.

Other Embodiments

The present disclosure can be implemented by processing including supplying a program implementing one or more functions of the aforementioned embodiments to a system or an apparatus over a network or through a storage medium and reading and executing the program by one or more processors in a computer in the system or the apparatus. Alternatively, it can be implemented by a circuit (such as an ASIC) implementing the one or more functions.

The present disclosure is applicable to a system including a plurality of apparatuses or an apparatus including one device. For example, a part of the module implemented by the system software 351 can be implemented by an external server, and a result processed by the external server may be obtained to implement the function.

The present disclosure is not limited to the aforementioned embodiments. Various changes, modifications, and alterations based on the spirit of the present invention (including organic combinations of embodiments) may be made and are not excluded from the scope of the present invention. In other words, configurations acquired by combining embodiments and variation examples thereof are also included in the present invention.

The abbreviations appearing in the descriptions of the aforementioned embodiments are defined as follows. ASIC stands for Application Specific Integrated Circuit. CPU stands for Central Processing Unit. FAX stands for facsimile. LAN stands for Local Area Network. MFP stands for multi function peripheral. PC stands for personal computer. PDL stands for Page Description Language. RAM stands for random-access memory. ROM stands for read only memory. SFP stands for single function peripheral. UI stands for user interface. USB stands for universal serial bus. IF stands for Interface.

The aforementioned embodiments provides a paper management system which can list and paper information pieces for each group registered by a user and associate it with a paper-feed stage.

In order to solve the problem that is it difficult to find a desired paper information piece from a list of a large number of registered paper information pieces, a paper management system is provided which enables easy selection of a paper information to be associated with a paper-feed stage.

In a printing factory having many registered paper information pieces, a combination of paper information pieces to be used for each customer to which printed materials are delivered may often be fixed. In view of this point, paper information pieces can be listed for each group such as a customer.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to embodiments, it is to be understood that the invention is not limited to the disclosed embodiments. The scope of the following claims is to be accorded the broadest interpretation so as to encompass all such modifications and equivalent structures and functions.

This application claims the benefit of Japanese Patent Application No. 2017-202093 filed Oct. 18, 2017, which is hereby incorporated by reference herein in its entirety.

What is claimed is:
1. A sheet information display system comprising:
   a display configured to display a plurality of pieces of sheet information;
   a user interface configured to select sheet information from among the plurality of pieces of sheet information displayed by the display; and
   a controller configured to perform an instruction for registering, for a sheet holder of a printing apparatus, the selected sheet information, wherein the sheet information display system is configured to group the plurality of pieces of sheet information into a plurality of groups, where each of the plurality of groups is able to have two or more pieces of sheet information, wherein, in a case where the plurality of pieces of sheet information is grouped into the plurality of groups, the user interface selects a group from among the plurality of groups, wherein the display displays, based on the group selected by the user interface, one or more pieces of sheet information belonging to the selected group without displaying one or more pieces of sheet information belonging to another group which is not selected by the user interface, wherein the display is configured to display sheet information included in each of the plurality of pieces of sheet information together with an icon, wherein the plurality of groups includes at least a first group and a second group that is different from the first group, and wherein the display is configured to display different icons, registered by a user, for sheet information registered in the first group by the sheet information display system and sheet information registered in the second group registered by the sheet information display system.

2. The sheet information display system according to claim 1, wherein the user interface further is configured to designate sheet information from among the plurality of pieces of sheet information and designate a group from among the plurality of groups, and wherein the sheet information display system registers, in the designated group, the sheet information designated by the user interface.

3. The sheet information display system according to claim 1, wherein, for each piece of sheet information, the user interface further is configured to select an icon to display together with each piece of sheet information included in the plurality of pieces of sheet information.

4. The sheet information display system according to claim 1, wherein the display is configured to display different icons for sheet information registered only in a single group of the plurality of groups by the sheet information display system and sheet information registered in at least two of the plurality of groups by the sheet information display system.

5. The sheet information display system according to claim 1, wherein the sheet information display system is configured to communicate with the printing apparatus.

6. A method for controlling a sheet information display system, the method comprising:

displaying a plurality of pieces of sheet information;

selecting sheet information from among the plurality of pieces of displayed sheet information; and performing an instruction for registering, for a sheet holder of a printing apparatus, the selected sheet information, wherein the plurality of pieces of sheet information is able to be grouped into a plurality of groups, where each of the plurality of groups is able to have two or more pieces of sheet information, wherein, in a case where the plurality of pieces of sheet information is grouped into the plurality of groups, selecting includes selecting a group from among the plurality of groups, wherein displaying includes displaying, based on the selected group, one or more pieces of sheet information belonging to the selected group without displaying one or more pieces of sheet information belonging to another group which is not selected, wherein displaying includes displaying sheet information included in each of the plurality of pieces of sheet information together with an icon, wherein the plurality of groups includes at least a first group and a second group that is different from the first group, and wherein displaying includes displaying different icons, registered by a user, for sheet information registered in the first group by the sheet information display system and sheet information registered in the second group registered by the sheet information display system.

7. A non-transitory computer readable storage medium for storing a computer program for causing a computer to perform a method for controlling a sheet information display system, the method comprising:

displaying a plurality of pieces of sheet information;

selecting sheet information from among the plurality of pieces of displayed sheet information; and performing an instruction for registering, for a sheet holder of a printing apparatus, the selected sheet information, wherein the plurality of pieces of sheet information is able to be grouped into a plurality of groups, where each of the plurality of groups is able to have two or more pieces of sheet information, wherein, in a case where the plurality of pieces of sheet information is grouped into the plurality of groups, selecting includes selecting a group from among the plurality of groups, wherein displaying includes displaying, based on the selected group, one or more pieces of sheet information belonging to the selected group without displaying one or more pieces of sheet information belonging to another group which is not selected, wherein displaying includes displaying sheet information included in each of the plurality of pieces of sheet information together with an icon, wherein the plurality of groups includes at least a first group and a second group that is different from the first group, and wherein displaying includes displaying different icons, registered by a user, for sheet information registered in the first group by the sheet information display system and sheet information registered in the second group registered by the sheet information display system.

8. A sheet information display system comprising:

a display configured to display a plurality of pieces of sheet information;

a user interface configured to select sheet information from among the plurality of pieces of sheet information displayed by the display; and a controller configured to perform an instruction for registering, for a sheet holder of a printing apparatus, the selected sheet information, wherein the sheet information display system is able to set, to a favorite, sheet information designated by a user from among the plurality of pieces of sheet information, wherein the user interface selects a favorite from among a plurality of favorites, wherein the display displays, based on the favorite selected by the user interface, one or more pieces of sheet information belonging to the favorite which is selected by the user interface without displaying one or more pieces of sheet information belonging to another favorite which is not selected by the user interface, wherein the sheet information display system is able to set the selected sheet information to at least one selected favorite of a plurality of favorites, where each of the plurality of favorites is able to have two or more pieces of sheet information set, wherein the display is configured to display sheet information included in each of the plurality of pieces of sheet information together with an icon, wherein the plurality of favorites includes at least a first favorite and a second favorite that is different from the first favorite, and wherein the display is configured to display different icons, registered by a user, for each of sheet information registered in the first favorite by the sheet information display system and sheet information registered in the second favorite registered by the sheet information display system.

9. The sheet information display system according to claim 8, wherein the user interface is able to select the sheet information to be registered for the sheet holder of the printing apparatus from among the plurality of pieces of sheet information displayed by the display in a state that the one or more pieces of sheet information belonging to the favorite which is selected by the user interface is displayed without displaying the one or more pieces of sheet information belonging to the another favorite which is not selected by the user interface.

10. The sheet information display system according to claim 9, wherein the user interface further is configured to designate a favorite from among the plurality of favorites, and wherein the sheet information display system sets the sheet information designated by the user interface to the favorite designated by the user interface.

11. The sheet information display system according to claim 8, wherein the user interface further is configured to select an icon which is displayed together with each of sheet information registered in the first favorite by the sheet information display system and sheet information registered in the second favorite registered by the sheet information display system.

12. The sheet information display system according to claim 8, wherein the display is configured to display different icons for sheet information registered only in a single favorite of the plurality of favorites by the sheet information display system and sheet information registered in at least two of the plurality of favorites by the sheet information display system.

13. The sheet information display system according to claim 8, wherein the sheet information display system is configured to communicate with the printing apparatus.

14. A method for a sheet information display system, the method comprising:

displaying a plurality of pieces of sheet information;

selecting sheet information from among the plurality of pieces of displayed sheet information; and performing an instruction for registering, for a sheet holder of a printing apparatus, the selected sheet information, wherein sheet information designated by a user from among the plurality of pieces of sheet information is able to be set to a favorite, wherein selecting includes selecting a favorite from among a plurality of favorites, wherein displaying includes displaying, based on the selected favorite, one or more pieces of sheet information belonging to the selected favorite without displaying one or more pieces of sheet information belonging to another favorite which is not selected, wherein the selected sheet information is able to be set to at least one selected favorite of a plurality of favorites, where each of the plurality of favorites is able to have two or more pieces of sheet information set, wherein displaying includes displaying sheet information included in each of the plurality of pieces of sheet information together with an icon, wherein the plurality of favorites includes at least a first favorite and a second favorite that is different from the first favorite, and wherein displaying includes displaying different icons, registered by a user, for each of sheet information registered in the first favorite by the sheet information display system and sheet information registered in the second favorite registered by the sheet information display system.

\* \* \* \* \*